US012751906B2

(12) United States Patent
Lees et al.

(10) Patent No.: US 12,751,906 B2
(45) **Date of Patent: *Oct. 6, 2026**

(54) TOOTH WHITENING FILM, PROCESS OF MANUFACTURING THEREOF AND A METHOD OF USING SUCH A FILM

(71) Applicant: BSolve Limited, Glasgow (GB)

(72) Inventors: Amy Lees, Glasgow (GB); Sarah Lindsay Grant, Glasgow (GB); Ian Herbert Stevens, Glasgow (GB); Robert Crichton, Glasgow (GB); Mark Alexander Livingstone, Glasgow (GB); Moira Warnock, Glasgow (GB); John Edward Cullen, Glasgow (GB); Melanie Macfarlane, Glasgow (GB)

(73) Assignee: BSolve Limited, Glasgow (GB)

(*) Notice: Subject to any disclaimer, the term of this patent is extended or adjusted under 35 U.S.C. 154(b) by 925 days.

This patent is subject to a terminal disclaimer.

(21) Appl. No.: 17/605,346

(22) PCT Filed: Apr. 22, 2020

(86) PCT No.: PCT/GB2020/051000

§ 371 (c)(1),
(2) Date: Oct. 21, 2021

(87) PCT Pub. No.: WO2020/217054

PCT Pub. Date: Oct. 29, 2020

(65) Prior Publication Data

US 2022/0226218 A1 Jul. 21, 2022

(30) Foreign Application Priority Data

Apr. 23, 2019 (GB) ..................................... 1905667

(51) Int. Cl.

| | |
|---|---|
| ***A61K 8/49*** | (2006.01) |
| ***A61C 7/08*** | (2006.01) |
| ***A61C 19/06*** | (2006.01) |
| ***A61K 8/24*** | (2006.01) |
| ***A61K 8/34*** | (2006.01) |
| ***A61K 8/73*** | (2006.01) |
| ***A61K 8/81*** | (2006.01) |
| ***A61Q 11/00*** | (2006.01) |

(52) U.S. Cl.

CPC ................ *A61K 8/492* (2013.01); *A61C 7/08* (2013.01); *A61C 19/066* (2013.01); *A61K 8/24* (2013.01); *A61K 8/345* (2013.01); *A61K 8/73* (2013.01); *A61K 8/731* (2013.01); *A61K 8/8176* (2013.01); *A61Q 11/00* (2013.01); *A61K 2800/48* (2013.01)

(58) Field of Classification Search

CPC ......... A61Q 11/00; A61C 7/08; A61C 19/066; A61K 8/492; A61K 8/24; A61K 8/345; A61K 8/73; A61K 8/731; A61K 8/8176; A61K 2800/48

See application file for complete search history.

(56) References Cited

U.S. PATENT DOCUMENTS

| | | | | |
|---|---|---|---|---|
| 2003/0215403 A1 | 11/2003 | Joiner et al. | | |
| 2006/0177383 A1* | 8/2006 | Gebreselassie | A61K 8/11 | 424/49 |
| 2008/0233541 A1 | 9/2008 | De Vreese et al. | | |
| 2009/0010970 A1 | 1/2009 | Velada | | |
| 2023/0210729 A1* | 7/2023 | Cullen | A61K 8/0241 | 424/57 |
| 2023/0310284 A1* | 10/2023 | Cullen | A61Q 11/00 | 433/216 |

FOREIGN PATENT DOCUMENTS

| | | | |
|---|---|---|---|
| EP | 1854457 A1 | 11/2007 | |
| JP | 2000281548 A | 10/2000 | |
| JP | 200881424 A | 4/2008 | |
| KR | 20020045224 A | 6/2002 | |
| KR | 20020097297 A | 12/2002 | |
| WO | WO-03009824 A1 | 2/2003 | |
| WO | WO-2005123024 A1 | 12/2005 | |
| WO | WO-2006107334 A1 | 10/2006 | |

(Continued)

OTHER PUBLICATIONS

Ier Francesco Porciani, et al, Whitening Effect by Stain Inhibition from a Chewing Gum with Sodium Hexametaphosphate in a Controlled Twelve-Week Single-Blind Trial, 17 J Clin. Dent. 1 (Year: 2006).*

(Continued)

*Primary Examiner* — Sean M Basquill
(74) *Attorney, Agent, or Firm* — MOSER TABOADA

(57) ABSTRACT

The present invention provides a tooth whitening film. The tooth whitening film comprises a dental bleaching agent comprising one or both of a non-hydrogen peroxide bleaching agent and hydrogen peroxide in a hydrogen peroxide-polymer complex, one or more polyphosphates, said one or more polyphosphates comprising one or more cyclic polyphosphates, one or more water soluble film-forming polymers, one or more plasticizers and one or more emulsifiers, wherein the film has a thickness from about 50 μm to about 500 μm. A kit comprising one or more such films having a thickness from about 50 μm to about 150 μm and a dental aligner is also provided. A process for the manufacture of the film is also provided, together with a method of using such a film to bleach teeth.

20 Claims, 3 Drawing Sheets

(56) References Cited

FOREIGN PATENT DOCUMENTS

| | | | | |
|---|---|---|---|---|
| WO | WO-2006127053 A2 | | 11/2006 | |
| WO | WO-2012002945 A1 | * | 1/2012 | ............... A61K 8/02 |
| WO | WO-2013106012 A1 | | 7/2013 | |
| WO | WO-2013162404 A1 | * | 10/2013 | ........... A61K 6/0023 |
| WO | WO-2015094333 A1 | | 6/2015 | |
| WO | WO 2016/064882 A1 | | 4/2016 | |
| WO | WO-2016100442 A1 | | 6/2016 | |
| WO | WO-2020217054 A1 | | 10/2020 | |

OTHER PUBLICATIONS

R. P. Shellis, et al, In Vitro Studies on the Effect of Sodium Tripolyphosphate on the Interactions of Stain and Salivary Protein with Hydroxyapatite, 33 J Dent. 313 (Year: 2005).*

UK Patent Office Search Report for application No. GB1905667.0 dated Sep. 12, 2019.

International Search Report and Written Opinion for Application No. PCT/GB2020/051000 dated Sep. 16, 2020.

* cited by examiner

TOOTH WHITENING FILM, PROCESS OF MANUFACTURING THEREOF AND A METHOD OF USING SUCH A FILM

FIELD OF THE INVENTION

The present invention provides a tooth whitening film. A process for the manufacture of the film is also provided, together with a method of using such a film to bleach teeth.

BACKGROUND

Human teeth naturally exhibit a variety of colours, which can be influenced by a number of factors, such as diet and medication. For instance, a number of foods, such as berries, and drinks, such as tea and red wine, contain chromogens which can stain teeth. Tobacco may also darken teeth. Other substances, such as acidic fruits and drinks, can promote staining by eroding dental enamel, softening teeth and making it easier for chromogens to attach. Consequently, there is a desire to whiten teeth to remove such staining.

Peroxides are a class of chemical compounds containing an oxygen-oxygen single bond which has a bleaching effect upon organic substances. Commonly, such compounds release hydrogen peroxide as the active bleaching agent upon contact with water present in saliva. Hydrogen peroxide may adversely affect teeth by increasing their sensitivity and/or the oral mucosa by irritating soft tissue such as gums. It is therefore desirable to enhance the peroxide bleaching effect without increase the concentration of peroxides used.

There is therefore a need for a tooth whitening film with an enhanced bleaching effect of the peroxide bleaching agent. There is also a need for a tooth whitening film which provides improved stain resistance to teeth.

SUMMARY OF INVENTION

In a first aspect, there is provided a tooth whitening film comprising:

- a dental bleaching agent comprising one or both of a non-hydrogen peroxide bleaching agent and hydrogen peroxide in a hydrogen peroxide-polymer complex;
- one or more polyphosphates, said one or more polyphosphates comprising one or more cyclic polyphosphates;
- one or more water soluble film-forming polymers;
- one or more plasticizers; and
- one or more emulsifiers, wherein the film has a thickness from about 50 μm to about 500 μm.

In one embodiment, the dental bleaching agent comprises a non-hydrogen peroxide bleaching agent, wherein the non-hydrogen peroxide bleaching agent comprises a peroxy carboxylic acid of formula (I):

$$R^1—R^2_n-C(=O)—O—O—H \quad (I)$$

in which:

$R^1$ is a monovalent organic group;

$R^2$ is a divalent organic bridging group; and n is 0 or 1.

When n is 0, $R^2$ is absent and the $R^1$ group is directly bound to the —C(=O)—O—O—H group. When n is 1, $R^2$ is present. The $R^1$ and $R^2$ groups may be independently substituted by from 1 to 6 substituent groups selected from oxygen in the form of a carbonyl group, hydroxyl or halo, particularly F or Cl.

In one embodiment, the monovalent organic group $R^1$ is selected from a $C_{1-10}$ alkyl group; a $C_{6-10}$ aryl group; and a heteroaryl group having from 5 to 10 atoms in the ring system, said ring system atoms selected from C, N, O and S; and $R^2$ the divalent organic bridging group is a substituted or unsubstituted $C_{1-10}$ alkylene group in which $R^1$ and $R^2$ may be independently substituted by from 1 to 6 substituent groups selected from oxygen in the form of a carbonyl group, hydroxyl or halo, such as F or Cl.

In a preferred embodiment, the peroxy carboxylic acid is 6-phthalimido peroxy caproic acid (also called ε-phthalimido peroxy hexanoic acid, PAP).

In another embodiment, the dental bleaching agent comprises a hydrogen peroxide-polymer complex. The polymer in the polymer complex may be a carbonyl containing polymer. The polymer complex may be a water soluble film-forming polymer discussed below.

Preferably the polymer in the polymer complex may be a polyvinyl pyrrolidone. Thus, the hydrogen peroxide-polymer complex may be a hydrogen peroxide-polyvinyl pyrrolidone complex. For instance, hydrogen peroxide can form hydrogen bonds with the carbonyl group of a pyrrolidone group to form the hydrogen peroxide-polymer complex. One hydrogen peroxide molecule may form a hydrogen bond with at least one carbonyl group of the pyrrolidone. Typically, one hydrogen peroxide molecule forms a hydrogen bond with one carbonyl group or one hydrogen peroxide molecule forms two hydrogen bonds, each bond with the carbonyl group of two adjacent pyrrolidone rings. Thus, the molar ratio of pyrrolidone groups to hydrogen peroxide in such a complex may be in the range of about 1:1 to 2:1. This results in complexes which may comprise from 15 to 20 wt. % by weight hydrogen peroxide and from 80 to 85 wt. % by weight polyvinyl pyrrolidone depending upon the degree of coordination between hydrogen peroxide and carbonyl groups.

In another embodiment, the dental bleaching agent comprises a non-hydrogen peroxide bleaching agent and a hydrogen peroxide-polymer complex.

The dental bleaching agent may be present in the film in a total amount of about 0.01% to about 35% by weight in terms of the non-hydrogen peroxide bleaching agent and hydrogen peroxide present by weight. Preferably, the dental bleaching agent may be present in a total amount of about 5% to about 20% by weight, more preferably in a total amount of about 8% to about 15% by weight.

As used herein, the term "by weight", unless specified otherwise, represents weight percent by dry weight of the film alone i.e. without any backing sheet or support.

In one embodiment, the one or more cyclic polyphosphates are defined by formula (II):

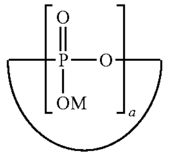

(II)

in which a is a whole number from 3 to 10. Preferably a is a whole number from 4 to 8. More preferably a is 6. M is selected from one or more of the group comprising hydrogen and an alkali metal. Preferred alkali metals comprise one or both of Na and K, more preferably Na.

Preferably, the one or more cyclic polyphosphates comprise sodium hexametaphosphate.

The one or more cyclic polyphosphates may be present in the film in a total amount of from about 2% to about 9% by weight. Preferably the one or more cyclic polyphosphates may be present in a total amount of from about 3% to about 7% by weight.

In one embodiment, the one or more polyphosphates may further comprise one or more linear polyphosphates. The one or more linear polyphosphates may comprise a compound of formula (III):

(III)

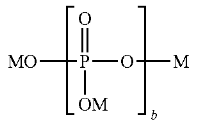

in which b is a whole number from 2 to 5. Preferably b is 3 or 4. Still more preferably, b is 3. M is selected from one or more of the group comprising hydrogen and an alkali metal. Preferred alkali metals comprise one or both of Na and K, more preferably Na. For the avoidance of doubt, substituent M of formulae (II) and (III) may be selected independently, although in a preferred embodiment they may be the same, such as Na.

Preferably, the one or more linear polyphosphates are selected from the group comprising sodium dipolyphosphate, sodium tripolyphosphate and sodium tertrapolyphosphate. More preferably, the one or more linear polyphosphates comprises sodium tripolyphosphate.

The one or more linear polyphosphates may be present in the film in a total amount of from 1% to 6% by weight. Preferably the one or more linear polyphosphates may be present in a total amount of from 2% to 5% by weight. More preferably the one or more linear polyphosphates may be present in a total amount of from 3% to 4% by weight. Still more preferably, the one or more linear polyphosphates may be present in a total amount of about 3.5% by weight.

In a preferred embodiment, the one or more polyphosphates comprise sodium hexametaphosphate and sodium tripolyphosphate. Preferably sodium hexametaphosphate is present in the film an amount of from 2% to 9% by weight and sodium tripolyphosphate is present in an amount of from 1% to 5% by weight. More preferably sodium hexametaphosphate is present in an amount of from 3% to 7% by weight and sodium tripolyphosphate is present in an amount of from 2% to 5% by weight. Still more preferably sodium hexametaphosphate is present in an amount of from 3% to 6% by weight and sodium tripolyphosphate is present in an amount of from 3% to 4% by weight.

In one embodiment, the water soluble film-forming polymer comprises one or more of a polyvinyl pyrrolidone, polyacrylic acid or a salt thereof, polyalkylene glycol in which the alkylene group has 2 or 3 carbon atoms and copolymers thereof, and a polysaccharide.

The polysaccharide water soluble film-forming polymer may be one or more of the group comprising pullulan, pectin, starch, dextrin, chitosan, alginic acid, salts of alginic acid and cellulose derivatives. Suitable cellulose derivatives include carboxyalkyl cellulose or a salt thereof and hydroxyalkyl cellulose or a salt thereof, in which the alkyl group of the carboxyalkyl cellulose or the hydroxyalkyl cellulose is independently selected from $C_{1-5}$ alkyl, preferably methyl, ethyl or propyl. A preferred hydroxyalkyl cellulose is hydroxypropyl cellulose.

Preferably the water soluble film-forming polymer may be selected from the group comprising polyvinyl pyrrolidone, pullulan, pectin, starch, carboxyalkyl cellulose or a salt thereof, hydroxyalkyl cellulose or a salt thereof, in which the alkyl group is independently selected from $C_{1-5}$ alkyl, alginic acid, salt of alginic acid, polyalkylene glycol in which the alkylene group has 2 or 3 carbon atoms and copolymers thereof, polyacrylic acid or a salt thereof and combinations thereof.

The water soluble film-forming polymer may be the polymer in the hydrogen peroxide-polymer complex which can form the dental bleaching agent. For instance, when the water soluble film-forming polymer is a polyvinyl pyrrolidone, it may be present in a complex with hydrogen peroxide as the dental bleaching agent.

The one or more film forming polymers may be present in the film in a total amount of from about 40% to about 95% by weight. Preferably, the one or more film forming polymers may be present in a total amount of from about 50% to about 90% by weight. More preferably, the one or more film forming polymers may be present in a total amount of from about 60% to about 85% by weight. Still more preferably, the one or more film forming polymers may be present in a total amount of from about 65% to about 80% by weight.

In one embodiment, the one or more plasticizers are selected from the group comprising a polyol such as glycerol, polyalkylene glycol, polyalkylene glycol monomethyl ether, monosaccharide, oligosaccharide, sorbital and sorbitan, in which the alkylene groups are independently selected from from $C_{1-5}$ alkylene, preferably methylene, ethylene or propylene. Preferred polyalkylene glycols are one or both of polyethylene glycol and polypropylene glycol. A preferred polyalkylene glycol monomethyl ether is polyethylene glycol monomethyl ether. A preferred plasticizer is glycerol.

The one or plasticizers may be present in the film in a total amount of from about 0.1% to about 15% by weight. Preferably the one or plasticizers may be present in a total amount of from about 1% to about 12% by weight. More preferably, the one or plasticizers may be present in the film in a total amount of from about 3% to about 10% by weight.

The tooth whitening film comprises one or more emulsifiers. In one embodiment, the one or more emulsifiers may be selected from ionic emulsifiers and non-ionic emulsifiers. In another embodiment the one or more emulsifiers may be selected from the group comprising a fatty acid derivative, a lecithin and a polysorbate Preferably the emulsifier, such as the non-ionic emulsifier, is selected from the group comprising a saturated fatty acid derivative, a lecithin or a polysorbate. The fatty acids may be saturated or unsaturated. More preferably the non-ionic emulsifier comprises one or both of at least one unsaturated fatty acid such as oleic acid and/or linoleic acid and optionally at least one saturated fatty acid such as palmitic acid and/or stearic acid or a polysorbate.

More preferred emulsifiers, such as non-ionic emulsifiers, are selected from fatty acids, which may be saturated or unsaturated and a polysorbate. More preferably the emulsifier, such as the non-ionic emulsifier, comprises one or both of (i) at least one unsaturated fatty acid such as oleic acid and/or linoleic acid and optionally at least one saturated fatty acid such as palmitic acid and/or stearic acid and (ii) a polysorbate. A polysorbate is a polyethoxylated ester of sorbital, sorbitan and isosorbide. Preferred saturated fatty acid derivatives include sucrose esters of saturated fatty acids; mono-, di- or tri-glycerides of saturated fatty acids; or sorbitan esters of saturated fatty acids.

The one or more emulsifiers may be present in the film in a total amount of from 0.1% to 10% by weight. Preferably the one or more emulsifiers are present in a total amount of from 1% to 5% by weight, more preferably from 2% to 4% by weight.

In one embodiment, the tooth whitening film may further comprise water. The water may be present in the film in an amount of less than or equal to 15% by weight, particularly from 0.1% to 15% by weight. Typically, the tooth whitening film may further comprise water in an amount of from 3% to 12% by weight, preferably from 5% to 10% by weight.

In one embodiment, the tooth whitening film may further comprise one or more optional components selected from the group comprising colourant, gelling agent, flavouring, sweetener, acidifier, antioxidant and chelating agent.

The colourant may be FD & C blue no. 1 or lakes thereof.

The gelling agent may be a hydrocolloid adhesive agent.

Other components of the tooth whitening film, such as some types of water soluble film forming polymer like polyvinyl pyrrolidone and certain polysaccharides like hydroxypropyl cellulose may exhibit gelling. For the purpose of the present disclosure, when a gelling agent is present as an optional further component of the tooth whitening film, this is considered separately from, and in addition to any of the other components which may exhibit gelling behaviour.

The flavouring may be selected from the group comprising menthol, peppermint and an alkyl alkanoates, in which the alkyl group may be straight chained or branched and may comprise from 1 to 8 carbon atoms, and the alkanoate group may comprise from 1 to 5 carbon atoms.

The sweetener may be selected from one or more of the group comprising aspartame, acesulfame K, sucralose, cyclamate, erythritol, mannitol, sorbital and xylitol.

The acidifier may be phosphoric acid.

The antioxidant may be one or more selected from the group comprising tocopherol (vitamin E), tertiary-butylhydroquinone (TBHQ), butylated hydroxyanisole (BHA) butylated hydroxytoluene and ethylenediaminetetraacetic acid or a salt thereof.

The chelating agent may be ethylenediaminetetraacetic acid or a salt thereof. Chelating agents can be used to sequester heavy metal ions, thereby preventing the degradation of peroxy carboxylic acids.

In another embodiment, the tooth whitening film may be a single layer. In a further embodiment, the tooth whitening film is free of any other layer or layers such as barrier layers or supporting substrates.

In another embodiment, the film, which may be used without a dental aligner, has a thickness in the range of from 50 to 250 micrometers, more preferably the film has a thickness in the range of from 100 to 200 micrometers, still more preferably about 150 micrometers.

Preferably, the film, which may be used without a dental aligner, has a length of from 50 to 70 mm, more preferably about 60 mm. Preferably the film has a width of from 15 to 20 mm, more preferably about 17.5 mm.

The film, which may be used without a dental aligner, may have a weight in the range of from 80 to 250 mg, preferably from 130 to 200 mg, more preferably about 150 mg.

In another embodiment, the film, which may be used with a dental aligner, has a thickness in the range of from 50 to 150 micrometers, more preferably the film has a thickness in the range of from 60 to 130 micrometers, still more preferably from 70 to 125 micrometers.

Preferably, the film, which may be used with a dental aligner, has a length of from 40 to 70 mm, more preferably from 50 to 60 mm. Preferably the film has a width of from 8 to 20 mm, more preferably from 10 to 12 mm.

The film, which may be used with a dental aligner, may have a weight in the range of from 80 to 200 mg, preferably from 90 to 160 mg.

In a second aspect, there is provided a process for the manufacture of a tooth whitening film, the process comprising at least the steps of:

mixing a dental bleaching agent comprising one or both of a non-hydrogen peroxide bleaching agent and hydrogen peroxide in a hydrogen peroxide-polymer complex in a total amount of about 0.01% to about 35% by weight of non-hydrogen peroxide bleaching agent and hydrogen peroxide, one or more polyphosphates in a total amount of about of about 3% to about 14% by weight, said one or more polyphosphates comprising one or more cyclic polyphosphates, one or more water soluble film-forming polymers in a total amount of about 40% to about 80% by weight, one or more plasticizers in a total amount of about 0.25% to about 15% by weight and one or more emulsifiers in a total amount of about 0.1% to about 10% by weight, with water to provide an aqueous tooth whitening liquid;

applying the aqueous tooth whitening liquid to a substrate to provide a substrate carrying the aqueous tooth whitening liquid;

drying the aqueous tooth whitening liquid to provide a tooth whitening film on the substrate, said film having a thickness from about 50 μm to about 500 μm.

Levels of polyphosphate above 15% by weight were found to result in a loss in the stability of the aqueous tooth whitening liquid. This effect started to occur when the loading of the polyphosphate in the aqueous tooth whitening liquid was increased above 10% by weight. The casting liquids with a polyphosphate content above 15% by weight exhibited a tendency to gel and provided a casting liquid that could not be cast shortly after the addition of polyphosphate.

In one embodiment, the aqueous tooth whitening liquid comprises greater than 60 wt. % water (on the basis of the total weight of the tooth whitening liquid, which includes the water present), preferably from 70 wt. % to 85 wt. % water. Thus, the aqueous tooth whitening liquid may comprise 40 wt. % or less of the components forming the tooth whitening film, preferably from 15 wt. % to 30 wt. %.

In one embodiment, the drying step comprises:

drying the aqueous tooth whitening liquid in air at a temperature of less than 60° C.

In a further embodiment the drying of the aqueous tooth whitening liquid in air is carried out at a temperature in the range of from 40 to less than 60° C., preferably from 40 to 55° C. In a further embodiment, the drying may be carried out at a rate in the range of from 0.2 to 2.0 m/min, preferably in a range of from 0.5 to 1.5 m/min, for instance by passing the aqueous tooth whitening liquid on the substrate through a dryer, such as a drying oven, hot air stream etc.

In a further embodiment, the drying step is carried out for a period of 80 minutes or less, preferably for a period of 35 minutes or less, more preferably for a period of 25 minutes or less. The drying step may be carried out for a period of at least 8 minutes, preferably for a period of at least 15 minutes, more preferably for a period of at least 20 minutes. Thus, the drying step may be carried out for a period of from 8 to 80 minutes, preferably from 15 to 35 minutes and more preferably from 20 to 25 minutes.

In another embodiment, the mixing step may be carried out under high shear, for instance at a shear rate of greater than 500 $s^{-1}$, preferably greater than 1000 $s^{-1}$, up to a maximum of 8000 $s^{-1}$. Preferably the shear rate is in a range of from 1000 $s^{-1}$ to 4000 $s^{-1}$.

In one embodiment, the mixing step further comprises mixing one or more further components selected from the group comprising colourant, gelling agent, flavouring, sweetener, acidifier, antioxidant and chelating agent.

In another embodiment, the process further comprises, between the mixing and applying steps, the step of:

degassing the aqueous tooth whitening liquid to provide a degassed aqueous tooth whitening liquid.

The degassing step may be carried out after the mixing of the components of the tooth whitening film with water and before the step of applying of the degassed aqueous casting liquid to the substrate.

In another embodiment, the process further comprises the step of:

separating the tooth whitening film from the substrate.

In a third aspect, there is provided a tooth whitening film obtainable by the process of the second aspect and its embodiments.

In a fourth aspect, there is provided a method of bleaching teeth, said method comprising at least the step of:

applying a tooth whitening film according to the first or third aspects to one or more teeth of a subject.

The method may be a cosmetic method, particularly a solely cosmetic method.

In one embodiment, the film is applied to one or more teeth of a subject for a period of more than 5 minutes and less than or equal to 60 minutes. Preferably the tooth whitening film is applied for a period of from 15 to 30 minutes.

The film may be applied to the front surface of one or more teeth and/or over the front surface of one or more teeth, chewing and back surfaces of one or more teeth.

The method may further comprise the step of applying a dental aligner to one or more teeth of a subject after the step of applying the tooth whitening film. Thus, the tooth whitening film may lie between the teeth and the dental aligner. Preferably, the dental aligner is a clear dental aligner.

When used with a dental aligner, the film is applied to one or more teeth of a subject for a period of more than 5 minutes and less than or equal to 120 minutes. Preferably the tooth whitening film is applied for a period of from 45 to 90 minutes.

In a fifth aspect there is provided a kit comprising a dental aligner and one or more tooth whitening films according to the first aspect in which the film has a thickness in the range of from 50 to 150 micrometers. Preferably the dental aligner is a clear dental aligner.

Preferably the film has a thickness in the range of from 60 to 130 micrometers, more preferably from 70 to 125 micrometers.

Preferably, the film has a length of from 40 to 70 mm, more preferably from 50 to 60 mm. Preferably the film has a width of from 8 to 20 mm, more preferably from 10 to 12 mm.

Such a film may have a weight in the range of from 80 to 200 mg, preferably from 90 to 160 mg.

BRIEF DESCRIPTION OF DRAWINGS

Embodiments of the present invention will now be described, by way of example only, with reference to the accompanying drawings in which.

DETAILED DESCRIPTION

Figure 1:
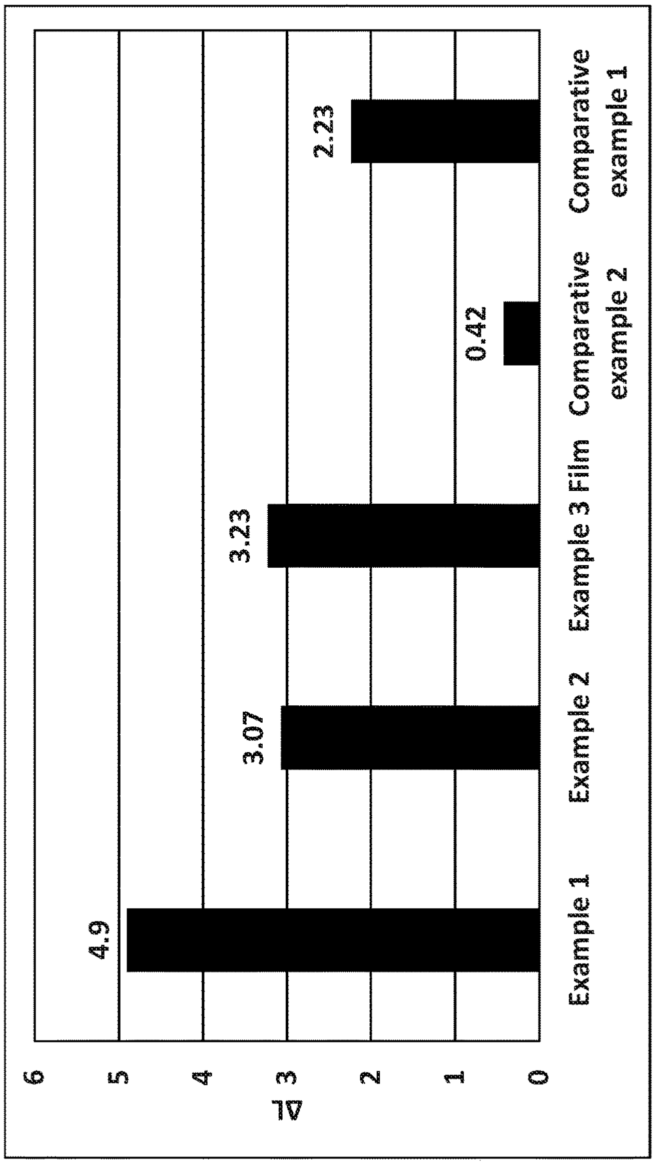
FIG. 1 shows a chart of the change in the extrinsic stain on teeth after 14 applications of tooth whitening films containing polyphosphate according to the invention (Examples 1-3) compared to two Comparative Examples (nos. 1 and 2) which are free of polyphosphate, for formulations in which the non-hydrogen peroxide bleaching agent was PAP.

Dental bleaching agents, such non-peroxides such as PAP, and hydrogen peroxide-polymer complexes are advantageous because they are environmentally friendly and are safe for use in humans, while still exhibiting high bleaching efficiency. However, it has been found that increasing concentrations of teeth whitening agents such as hydrogen peroxide may increase tooth or gum sensitivity and that it would be advantageous to obtain effective teeth whitening at lower concentrations of the bleaching agent.

The tooth whitening film described herein comprises a dental bleaching agent comprising one or both of a non-hydrogen peroxide bleaching agent and hydrogen peroxide in a hydrogen peroxide-polymer complex; one or more polyphosphates, in which the one or more polyphosphates comprise one or more cyclic polyphosphates; one or more water soluble film-forming polymers; one or more plasticizers; and one or more emulsifiers, and the film has a thickness from about 50 μm to about 500 μm.

Furthermore, the tooth whitening film described herein may be used in combination with a dental aligner. Thus, a kit comprising a dental aligner and one or more tooth whitening films for use with the dental aligner is also provided.

Clear dental aligners are increasingly used in orthodontic procedures to straighten teeth in preference to traditional metallic braces. These aligners are clear plastic imprints of the teeth which are worn for up to approximately 20 hours per day for up to two years. The aligners are designed so that a new aligner is used every two weeks which has a slightly different positioning of the mould so that the teeth are gradually re-positioned over time into the desired conformation.

As aligners are in use for such a large part of each day, traditional out of dental office methods of whitening teeth such using a peroxide gel and gum shield are impractical as the dental aligner is already in place. Whitening strips with a backing liner are not practical as they can swell and cause pressure on the teeth and aligner and also the strip has to be removed post use, thus meaning that the dental aligner also has to be removed. Applying a tooth whitening gel or paste to the inside of the tray of the dental aligner and then placing this over the teeth is not practicable because the gel or paste is forced out of the aligner due to the tight fit between aligner and teeth.

It is therefore advantageous to provide a tooth whitening film which can be applied to the teeth with the aligner placed on top without interfering with the normal routine of teeth alignment and without impacting on its effectiveness. For this purpose, it is preferred that the film has a thickness of from 50 to 150 micrometers, more preferably from 60 to 130 micrometers, still more preferably from 70 to 125 micrometers. Such thicknesses allow the film to be placed between one or more teeth and the aligner, without interfering with or impacting upon the function of the aligner to straighten one or more teeth. It is also preferred that the film has a length of from 40 to 70 mm, more preferably from 50 to 60 mm. Preferably the film has a width of from 8 to 20 mm, more preferably from 10 to 12 mm. Such films may have a weight in the range of from 80 to 200 mg, preferably from 90 to 160 mg.

The present invention provides a tooth whitening film, which whether used with a dental aligner or not, comprises a cyclic polyphosphate and optionally a linear polyphosphate. Such a film provides one or both of enhanced bleaching and improved stain resistance. The film does not require the presence of further layers, such as barrier layers or supporting substrates. In addition, enhanced bleaching efficiency may be achieved at lower concentrations of the dental bleaching agent due to the presence of the polyphosphate. Also disclosed is a process for the manufacture of such a tooth whitening film and a method of using such a film.

The tooth whitening film may further comprise water. The water may be present in the film in an amount of less than 15% by weight, particularly from 0.1% to 15% by weight. Typically, the tooth whitening film may further comprise water in an amount of from 3% to 12% by weight, preferably from 5% to 10% by weight.

The tooth whitening film may further comprise one or more further components selected from the group comprising colourant, gelling agent, flavouring, sweetener, acidifier, antioxidant and chelating agent.

The tooth whitening film is defined in terms of the dry weight of the film i.e. the weight of components dried to exclude water, expressed as percentages (i.e. wt. %) by total dry weight of the film alone i.e. without any backing sheet or support. The proportions of the non-hydrogen peroxide dental bleaching agent and/or hydrogen peroxide, polyphosphate, water soluble film-forming polymer, plasticizer and emulsifier and optionally one or more further components, and optionally water, when expressed as percentages by weight of the dry film, should total 100 weight %.

The tooth whitening film is flexible such that it is mouldable to, and can adopt the surface shape of the teeth.

Dental Bleaching Agent

The tooth whitening film comprises a dental bleaching agent comprising one or both of a non-hydrogen peroxide bleaching agent and hydrogen peroxide in a hydrogen peroxide-polymer complex.

As used herein, the term "non-hydrogen peroxide bleaching agent" is a bleaching agent which does not comprise hydrogen peroxide ($H_2O_2$). The non-hydrogen peroxide bleaching agent may be a peroxide, in that it contains an oxygen-oxygen single bond, so long as the agent is not hydrogen peroxide or it may be another (non-hydrogen peroxide) organic or inorganic bleaching agent. However, the non-peroxide bleaching agent can release hydrogen peroxide upon contact with water.

As used herein, the term "hydrogen peroxide-polymer complex" is a dental bleaching agent comprising hydrogen peroxide in which the hydrogen peroxide is complexed with a polymer. For instance, hydrogen peroxide can form hydrogen bonds with the carbonyl group of a polymer, such as polyvinyl pyrrolidone, to form a complex. As such, the hydrogen peroxide-polymer complex does not contain free hydrogen peroxide. By 'free hydrogen peroxide' it is meant hydrogen peroxide which is not bound to another compound, such as complexed with another compound via hydrogen bonding.

The non-hydrogen peroxide bleaching agent may comprise a peroxy carboxylic acid. The peroxy carboxylic acid may have the formula (I):

$$R^1—R^2_n—C(═O)—O—O—H \quad (I)$$

in which:

- $R^1$ is a monovalent organic group. Preferably $R^1$ may be a $C_{1-10}$ alkyl group; a $C_{6-10}$ aryl group; and a heteroaryl group having from 5 to 10 atoms in the ring system, said ring system atoms selected from C, N, O and S. More preferably, $R^1$ is a N-phthalimido group;
- $R^2$ is a divalent organic bridging group and n is 0 or 1. When n is 0, $R^2$ is absent and the $R^1$ group is directly bound to the —C(═O)—O—O—H group. When n is 1, $R^2$ is present. $R^2$ is preferably a substituted or unsubstituted $C_{1-10}$ alkylene group. More preferably $R^2$ is a substituted or unsubstituted $C_{4-6}$ alkylene group, still more preferably $R^2$ is a pentylene group (i.e. $—(CH_2)_5—$).

The $R^1$ and $R^2$ groups may be independently substituted by from 1 to 6 substituent groups selected from oxygen in the form of a carbonyl group; hydroxyl; and halo, particularly F or Cl. For the avoidance of doubt, two hydrogen atoms can be removed from the same carbon atom and substituted with a single oxygen atom to form a carbonyl group.

In a preferred embodiment, the peroxy carboxylic acid is 6-phthalimido peroxy caproic acid (also called ε-phthalimido peroxy hexanoic acid, PAP).

Preferably a peroxy carboxylic acid bleaching agent, such as PAP, is present in a proportion of from 0.01 to 10% by dry weight of the tooth whitening film. More preferably the peroxy carboxylic acid bleaching agent, such as PAP, is present in a proportion of from 0.5 to 5.0% by dry weight of the tooth whitening film.

A peroxy carboxylic acid bleaching agent may be provided as a complex, such as a complex of peroxy carboxylic acid and a carbohydrate, for instance dextrin. Such complexes may comprise a proportion of from 1 to 20% peroxy carboxylic acid bleaching agent such as PAP, with the balance being carbohydrate such as dextrin. Typically, these complexes may comprise approximately from 10% by weight to 20% by weight, such as about 11% by weight or about 17% by weight peroxy carboxylic acid, such as PAP, with the balance being a carbohydrate, such as dextrin. Preferably the peroxy carboxylic acid bleaching agent is provided as a complex of PAP and dextrin. Examples of such complexes are those sold under the trade name EURECO™ by Solvay.

Complexes of a peroxy carboxylic acid, such as PAP, with a carbohydrate, such as dextrin, provide the bleaching agent with improved stability, particularly improved thermal and chemical stability. The bleaching agent is less reactive because it is intermolecularly bonded with the carbohydrate, such as within a dextrin ring, thereby providing a thermal energy barrier to degradation. Energy is required to dissociate the peroxy carboxylic acid from the complex before it can be degraded.

In aqueous acidic conditions, the peroxy carboxylic acid bleaching agent degrades slowly with the evolution of hydrogen peroxide. For instance, the peroxy carboxylic acid PAP degrades slowly to ε-phthalimido hexanoic acid (PAC). However, this is not the primary mechanism which provides the tooth whitening effect.

Instead, in alkaline conditions, such as that produced by saliva, a peroxy carboxylic acid bleaching agent degrades with the evolution of oxygen and water, rather than hydrogen peroxide. For instance, in alkaline conditions PAP degrades to PAC, oxygen and water. The rate and extent of degradation increases with increasing pH. An acidifier may be present in the tooth whitening film to stabilise a peroxy carboxylic acid non-hydrogen peroxide bleaching agent, such as PAP, and mitigate against its degradation prior to use.

Alternatively or additionally, the non-hydrogen peroxide bleaching agent may comprise sodium chlorite. Typically, sodium chlorite may be present in a proportion of from 1% to 5% by dry weight of the tooth whitening film.

Alternatively or additionally, the dental bleaching agent may comprise hydrogen peroxide in a hydrogen peroxide-polymer complex. The polymer in the polymer complex may be the water soluble film-forming polymer. For instance, hydrogen peroxide can form hydrogen bonds with the carbonyl group of a pyrrolidone group to form a complex. One hydrogen peroxide molecule may form a hydrogen bond with at least one carbonyl group of the pyrrolidone. Typically, one hydrogen peroxide molecule forms a hydrogen bond with one carbonyl group or one hydrogen peroxide molecule form two hydrogen bonds, each bond with the carbonyl group of two adjacent pyrrolidone rings. Thus, the molar ratio of pyrrolidone groups to hydrogen peroxide in such a complex may be in the range of about 1:1 to 2:1. This results in complexes which may comprise from 15 to 20 wt. % by weight hydrogen peroxide and from 80 to 85 wt. % by weight polyvinyl pyrrolidone depending upon the degree of coordination between hydrogen peroxide and carbonyl groups.

The polyvinyl pyrrolidone polymer in the complex may be one or more selected from the group comprising uncrosslinked polyvinyl pyrrolidone, crosslinked polyvinyl pyrrolidone, a copolymer of vinyl pyrrolidone and acrylic acid, a copolymer of vinyl pyrrolidone and vinyl acrylate, or alkylated polyvinyl pyrrolidone. The polyvinyl pyrrolidone may preferably have a weight average molecular weight in the range of from 1 million to 1.5 million, still more preferably about 1.3 million.

Suitable pyrrolidone polymer complexes with hydrogen peroxide are sold under the trade name Peroxydone™ by Ashland.

Preferably a hydrogen peroxide-polymer complex dental bleaching agent, such as a hydrogen peroxide-polyvinyl pyrrolidone complex, is present in a proportion of from 0.01 to 80% by dry weight of the tooth whitening film. For instance, 80% by dry weight of a hydrogen peroxide-polyvinyl pyrrolidone complex would correspond to 14.4% hydrogen peroxide and 65.6% polyvinyl pyrrolidone by dry weight of the film. More preferably the hydrogen peroxide-polymer complex, such as a hydrogen peroxide-polyvinyl pyrrolidone complex, is present in a proportion of from 10 to 70%, still more preferably from 20 to 60% by dry weight of the tooth whitening film.

As another example, the hydrogen peroxide-polymer complex may further comprise a hydrogen peroxide-urea complex, also called carbamide peroxide. This complex contains equal proportions of hydrogen peroxide and urea in which a hydrogen bond is formed between the oxygen of the hydrogen peroxide and the nitrogen of the primary amine of the urea.

The non-hydrogen peroxide dental bleaching agent and hydrogen peroxide may be present in the film in a total amount of about 0.01% to about 35% by weight. Preferably, the non-hydrogen peroxide dental bleaching agent and hydrogen peroxide may be present in a total amount of about 5% to about 20% by weight, more preferably in a total amount of about 8% to about 15% by weight.

For the avoidance of doubt, these proportions are defined in terms of the active component of the dental bleaching agent, i.e. the non-hydrogen peroxide dental bleaching agent and/or hydrogen peroxide, rather than, for instance, the proportion of the hydrogen peroxide-polymer complex present in the tooth whitening film. Thus, these proportions may refer to the dental bleaching agent active which may comprise or consist essentially of or consist of one or both of a non-hydrogen peroxide dental bleaching agent and hydrogen peroxide.

One or More Polyphosphates

The tooth whitening film comprises one or more polyphosphates including one or more cyclic polyphosphates. The one or more polyphosphates may be present in the film in a total amount of about of about 2% to about 15% by weight. Optionally, the one or more polyphosphates may further comprise one or more linear polyphosphates.

The one or more cyclic polyphosphates may comprise one or more metaphosphates. Metaphosphates are oxyanions of general formula $(PO_3^-)_n$, where n is a whole number ≥3. The metaphosphate anion may be charge balanced by a cationic counterion M, such as a cation of one or more of the group comprising hydrogen and an alkali metal, such that the neutral species has the general formula $M_n(PO_3)_n$ for a cation in oxidation state (I).

The one or more cyclic polyphosphates may be a metaphosphate defined by formula (II):

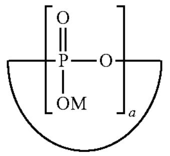

(II)

in which a is a whole number from 3 to 10. Preferably a is a whole number from 4 to 8. More preferably a is 6. M is selected from one or more of the group comprising hydrogen and an alkali metal. Preferred alkali metals are Na or K, more preferably Na.

For the avoidance of doubt, the one or more cyclic polyphosphates of formula (II) are defined by the repeat unit [—P(═O)(OM)-O—], with the term ‘a’ representing the number of repeat units present. The arc joining the two free bonds of the repeat unit of formula (II) is intended to represent the cyclic nature of the polyphosphate. The cyclic polyphosphate may thus be represented by the formula $M_a(PO_3)_a$. Thus, when a=6, a hexametaphosphate is provided.

When M is H, formula (II) provides a cyclic polyphosphoric acid. When M is an alkali metal, a cyclic polyphosphoric acid salt, such as a cyclic polyphosphate of formula (IIa) is provided:

(IIa)

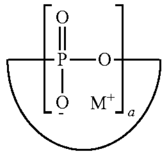

in which M is preferably a cation of an alkali metal. The cation of the alkali metal provides charge balance to the cyclic anionic polyphosphate. The alkali metal cation may have an oxidation state of (I). Preferably M is the cation of Na or K, more preferably Na.

Preferably, the one or more cyclic polyphosphates comprise sodium hexametaphosphate.

The one or more cyclic polyphosphates may be present in the film in a total amount of from about 2% to about 9% by weight. Preferably the one or more cyclic polyphosphates may be present in a total amount of from about 3% to about 7% by weight.

In one embodiment, the one or more polyphosphates may further comprise one or more linear polyphosphates. The one or more linear polyphosphates may comprise a compound of formula (II):

(III)

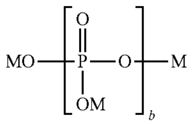

in which b is a whole number from 2 to 5. Preferably b is 3 or 4. Still more preferably, b is 3. M is a cation providing charge balance. M is preferably a cation of one or more of the group comprising hydrogen and an alkali metal i.e. a cation of oxidation state (I). Preferred alkali metal cations comprise those of Na or K, more preferably Na.

For the avoidance of doubt, the one or more linear polyphosphates of formula (III) are defined by the repeat unit [—P(═O)(OM)-O—], with the term 'b' representing the number of repeat units present. The linear polyphosphate may thus be represented by the formula $M_{b+2}O(PO_3)_b$. Thus, when b=3, a tripolyphosphate is provided.

When M is H, formula (III) provides a linear polyphosphoric acid. When M is an alkali metal, a linear polyphosphoric acid salt, such as a linear polyphosphate of formula (IIIa) is provided:

(IIIa)

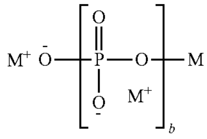

in which M is preferably a cation of an alkali metal. The cation of the alkali metal provides charge balance to the linear anionic polyphosphate. The alkali metal cation may have an oxidation state of (I). Preferably M is the cation of Na or K, more preferably Na. The terminal repeat unit [—P(═O)($O^-M^+$)-O—] may be alternatively represented as [—P(═O)($O^-M^+$)-$O^-$] with the anionic charge balanced by the cationic charge on M. Thus, O-]-M may not represent a covalent bond.

Preferably, the one or more linear polyphosphates are selected from the group comprising sodium dipolyphosphate, sodium tripolyphosphate and sodium tertrapolyphosphate. More preferably, the one or more linear polyphosphates comprises sodium tripolyphosphate.

The one or more linear polyphosphates may be present in the film in a total amount of from 1% to 6% by weight, with the proviso that the total amount of one or more polyphosphate is in the range of about 2% to about 15% by weight. Preferably the one or more linear polyphosphates may be present in a total amount of from 2% to 5% by weight. More preferably the one or more linear polyphosphates may be present in a total amount of from 3% to 4% by weight. Still more preferably, the one or more linear polyphosphates may be present in a total amount of about 3.5% by weight.

The one or more polyphosphates may comprise a cyclic polyphosphate, such as a metaphosphate, and a linear polyphosphate. Preferably the cyclic polyphosphate, such as a metaphosphate, is present in the film an amount of from 2% to 9% by weight and the linear polyphosphate is present in an amount of from 1% to 6% by weight. More preferably the cyclic polyphosphate, such as a metaphosphate, is present in an amount of from 3% to 7% by weight and the linear polyphosphate is present in an amount of from 2% to 5% by weight. Still more preferably the cyclic polyphosphate, such as a metaphosphate, is present in an amount of from 3% to 6% by weight and the linear polyphosphate is present in an amount of from 3% to 4% by weight.

The one or more polyphosphates may comprise sodium hexametaphosphate and sodium tripolyphosphate. Preferably sodium hexametaphosphate is present in the film an amount of from 2% to 9% by weight and sodium tripolyphosphate is present in an amount of from 1% to 6% by weight. More preferably sodium hexametaphosphate is present in an amount of from 3% to 7% by weight and sodium tripolyphosphate is present in an amount of from 2% to 5% by weight. Still more preferably sodium hexametaphosphate is present in an amount of from 3% to 6% by weight and sodium tripolyphosphate is present in an amount of from 3% to 4% by weight.

Water Soluble Film-Forming Polymer

The tooth whitening film comprises one or more water soluble film-forming polymers.

The water soluble film-forming polymer provides structure to the film and controls the release of the bleaching agent during tooth whitening. As used herein, a "water soluble" polymer is one in which one gram of polymer is soluble in 30 g or less of water. For instance, a polymer may be water soluble if 1 g of polymer is soluble in 25 g water.

The one or more water soluble film-forming polymers may be one or more selected from the group comprising a polyvinyl pyrrolidone, polyacrylic acid or a salt thereof, polyalkylene glycol in which the alkylene group has 2 or 3 carbon atoms and copolymers thereof, and a polysaccharide.

Examples of polysaccharide water soluble film-forming polymers include pullulan, pectin, starch, dextrin, chitosan, alginic acid, salts of alginic acid and cellulose derivatives. Suitable cellulose derivatives include carboxyalkyl cellulose or a salt thereof and hydroxyalkyl cellulose or a salt thereof, in which the alkyl group of the carboxyalkyl cellulose or the hydroxyalkyl cellulose is independently selected from $C_{1-5}$ alkyl, preferably methyl, ethyl or propyl. A preferred hydroxyalkyl cellulose is hydroxypropyl cellulose.

Preferably the water soluble film-forming polymer may be selected from the group comprising polyvinyl pyrrolidone, pullulan, pectin, starch, carboxyalkyl cellulose or a salt thereof, hydroxyalkyl cellulose or a salt thereof, in which the alkyl group is independently selected from $C_{1-5}$ alkyl, alginic acid, salt of alginic acid, polyalkylene glycol in which the alkylene group has 2 or 3 carbon atoms and copolymers thereof, polyacrylic acid or a salt thereof and combinations thereof. More preferably the water soluble film-forming polymer comprises polyvinyl pyrrolidone and one or more further water soluble film-forming polymer selected from the group comprising pullulan, pectin, starch, carboxyalkyl cellulose or a salt thereof, hydroxyalkyl cellulose or a salt thereof, in which the alkyl group is independently selected from $C_{1-5}$ alkyl, alginic acid, salt of alginic acid, polyethylene glycol, polypropylene glycol and copolymers of polyethylene glycol and polypropylene glycol, polyacrylic acid or a salt thereof.

The water soluble polymer may be selected from the group comprising polyvinyl pyrrolidone, hydroxylalkyl cellulose, hydroxyalkyl alkyl cellulose, carboxyalkyl cellulose, salts of carboxyalkyl cellulose, carbomer, dextrin, chitosan polyethylene glycol, polypropylene glycol and copolymers of polyethylene glycol and polypropylene glycol.

The polyvinyl pyrrolidone may be one or more selected from the group comprising uncrosslinked polyvinyl pyrrolidone, crosslinked polyvinyl pyrrolidone, a copolymer of vinyl pyrrolidone and acrylic acid, a copolymer of vinyl pyrrolidone and vinyl acrylate, or alkylated polyvinyl pyrrolidone. As used herein, the term “alkylated” PVP means PVP substituted with an alkyl group. For instance, the PVP may be alkyl substituted in the 3-position. The alkyl group may be a straight chain or branched $C_{1-5}$ alkyl. Exemplary alkyl groups include methyl and ethyl groups. As discussed above, polyvinyl pyrrolidone may be present in a complex with hydrogen peroxide as the dental bleaching agent.

The polyvinyl pyrrolidone may preferably have a weight average molecular weight in the range of from 1 million to 1.5 million, still more preferably about 1.3 million. Suitable polyvinyl pyrrolidone is sold under the trade name Kollidon™ by BASF.

The hydroxyalkyl cellulose may be one or both of hydroxyethyl cellulose and hydroxypropyl cellulose. With regard to the hydroxyalkyl alkyl cellulose, the hydroxyalkyl group may be independently selected from hydroxyethyl and hydroxypropyl while the alkyl cellulose may be independently selected from the group comprising methyl cellulose, ethyl cellulose and propyl cellulose. Preferably, the hydroxyalkyl cellulose is hydroxypropyl cellulose. Suitable hydroxypropyl cellulose is sold under the trade name Klucel™ by Ashland.

The carboxyalkyl cellulose or a salt thereof many be carboxymethyl cellulose or an alkali metal salt thereof, such as sodium. Preferably the carboxyalkyl cellulose salt is sodium carboxymethyl cellulose. Suitable sodium carboxymethyl cellulose is sold under the trade name Blanose™ by Hercules Inc.

Typically, when the water soluble film-forming polymer is polyalkylene glycol in which the alkylene group has 2 or 3 carbon atoms or copolymers thereof, the polymer or copolymer should have a molecular weight of less than or equal to 200 000, particularly in the range of from 20 000 to 200 000.

Certain water soluble film-forming polymers may also function as adhesives, aiding attachment of the tooth whitening film to one or more teeth. Such adhesive water soluble film-forming polymers may be one or more selected from the group comprising a carboxyalkyl cellulose, a salt of carboxyalkyl cellulose, carbomer, dextrin, chitosan and polyethylene glycol. Polyethylene glycol, also known as polyethylene oxide, is a preferred adhesive water soluble film-forming polymer.

When the adhesive water soluble film-forming polymer is a carboxyalkyl cellulose or a salt thereof, particularly an alkali metal salt, it is preferably a carboxy $C_{1-5}$alkyl cellulose, or its sodium salt. Most preferably, the adhesive water soluble polymer comprises carboxymethyl cellulose. The carboxymethyl cellulose may have a weight average molecular weight of from 49 000 to 725 000, typically about 95 000. Suitable sodium carboxymethyl celluloses are sold under the trade name Blanose™ by Ashland.

When the adhesive water soluble film-forming polymer is a carbomer, also known as poly(acrylic acid), it is preferably a homopolymer of acrylic acid; or a salt thereof, such as an alkali metal or an alkaline earth metal salt, preferably sodium or calcium.

When the adhesive water soluble film-forming polymer is a dextrin, it comprises polymers of D-glucose units linked by α-(1→4) or α-(1→6) glycosidic bonds.

When the adhesive water soluble film-forming polymer is chitosan, it comprises randomly distributed β-(1→4) linked D-glycosamine and N-acetyl-D-glucosamine.

The water soluble film-forming polymer preferably comprises a polyvinyl pyrrolidone and one or more adhesive water soluble polymers, such as those defined above. The water soluble film-forming polymer more preferably comprises polyvinyl pyrrolidone, hydroxypropyl cellulose and sodium carboxymethyl cellulose. Alternatively, the water soluble film-forming polymer preferably comprises a polyvinyl pyrrolidone and a carbohydrate, such as those defined above, particularly pectin.

The one or more film forming polymers may be present in the film in a total amount of from about 40% to about 95% by weight. Preferably, the one or more film forming polymers may be present in a total amount of from about 60% to about 90% by weight. More preferably, the one or more film forming polymers may be present in a total amount of from about 70% to about 85% by weight. Still more preferably, the one or more film forming polymers may be present in a total amount of from about 75% to about 80% by weight.

Plasticizer

A plasticizer is present in the tooth whitening film. Preferably the plasticizer should be a physiologically acceptable plasticizer.

The one or more plasticizers may be selected from the group comprising a polyol such as glycerol, polyalkylene glycol in which the alkylene groups are independently selected from from $C_{2-5}$ alkylene, polyalkylene glycol monomethyl ether in which the alkylene groups are independently selected from from $C_{2-5}$ alkylene, monosaccharide, oligosaccharide, sorbital and sorbitan, preferably ethylene or propylene. Preferred polyalkylene glycols are one or both of polyethylene glycol and polypropylene glycol. A preferred polyalkylene glycol monomethyl ether is polyethylene glycol monomethyl ether.

The plasticizer may be a hydrophilic plasticizer, such as one or more of the group comprising a polyol such as glycerol, polyethylene glycol, polyethylene glycol monomethyl ether, propylene glycol, sorbital and sorbitan. The preferred plasticizer is glycerol The one or plasticizers may be present in the film in a total amount of from about 0.1% to about 15% by weight. Preferably the one or plasticizers may be present in a total amount of from about 1% to about 12% by weight. More preferably, the one or plasticizers may be present in the film in a total amount of from about 3% to about 10% by weight. When the dental bleaching agent comprises a non-hydrogen peroxide dental bleaching agent, such as PAP, the plasticizer may be present in a range of from 1 to 5% by weight. When the dental bleaching agent comprises hydrogen peroxide in a hydrogen peroxide-polymer complex, the plasticizer may be present in a range of from 8 to 12% by weight.

Emulsifier

The tooth whitening film comprises one or more emulsifiers. The one or more emulsifiers may be selected from ionic emulsifiers and non-ionic emulsifiers.

Preferably the non-ionic emulsifier is selected from the group comprising a saturated fatty acid derivative, a lecithin or a polysorbate. The fatty acids may be saturated or unsaturated. More preferably the non-ionic emulsifier comprises one or both of at least one unsaturated fatty acid such as oleic acid and/or linoleic acid and optionally at least one saturated fatty acid such as palmitic acid and/or stearic acid or a polysorbate.

Polysorbates are polyethoxylated esters of sorbital, sorbitans and isosorbide. Preferred saturated fatty acid derivatives include sucrose esters of saturated fatty acids; mono-, di- or tri-glycerides of saturated fatty acids; or sorbitan esters of saturated fatty acids. A preferred emulsifier is Sorbital, such as T80 supplied by Azelis.

The one or more emulsifiers may be present in the film in a total amount of from 0.1 to 10% by dry weight of the tooth whitening film, preferably in the range of from 2.0 to 2.5% by weight.

Optional Components

The tooth whitening film may further comprise one or more optional components selected from the group comprising colourant, gelling agent, flavouring, sweetener, acidifier, antioxidant and chelating agent.

The colourant may be FD & C blue no. 1 or lakes thereof.

The gelling agent may be a hydrocolloid. Typically, the gelling agent may be a hydrocolloid which also functions as an adhesive agent. As used herein, the term "hydrocolloid" means a hydrophilic polymer, which may be of any origin such as plant, animal, microbial or synthetic, which contains hydrophobic groups and forms a gel in the presence of water, that is, a heterogeneous system with a solid hydrocolloid network containing a liquid water phase. The hydrocolloid adhesive agent may be selected from a natural gum, a polyacrylic acid or a poly alkylacrylic acid in which the alkyl group is methyl or ethyl. The alkyl group may be methyl or ethyl i.e. poly methacrylic acid or poly ethacrylic acid. The natural gum may be selected from alginic acid and its salts, agar, carrageenan, tragacanth and polysaccharide gums. More preferably, when the hydrocolloid gelling agent is a natural gum, it is tragacanth gum comprising a mixture of water-soluble and water-insoluble polymers, particularly polysaccharides, such as a mixture of tragacanthin and bassorin polymers. The bassorin polymer may be a polymer of fucose, xylose, arabinose, galacturonic acid and rhamnose.

Alternatively, the hydrocolloid adhesive agent may be a polymer of acrylic acid or an alkylacrylic acid as defined above. High molecular weight polyacrylic acid is also known as carbomer. Polymers of acrylic acid which may be either crosslinked or uncrosslinked. Examples of crosslinking agents include allyl ether pentaerythritol, allyl ethers of sucrose or ally ethers of propylene. Crosslinked polymers of acrylic acid are sold under the trade name Carbopol® by Lubrizol Corporation.

The polyacrylic acid may be provided as a salt, such as an ammonium, sodium, potassium, magnesium or calcium salt. Cross-linked polyacrylic acid, such as those cross-linked with divinyl glycol may be provided as salts such as magnesium or calcium salts, particularly calcium salts, also known as polycarbophils. Suitable polycarbophils are sold under the trade name Noveon™ by Lubrizol Corporation.

The gelling agent may be present in a range of from 0.1 to 10% by dry weight of the tooth whitening film.

The flavouring may be an artificial flavouring or a natural flavouring. The flavouring may be selected from the group comprising menthol, peppermint and an alkyl alkanoate, in which the alkyl group may be straight chained or branched and may comprise from 1 to 8 carbon atoms, and the alkanoate group may comprise from 1 to 5 carbon atoms. Preferably the alkyl group of the alkyl alkanoate has 1, 2, 5 or 8 carbon atoms and the alkanoate group of the alkyl alkanoate may comprise from 1 to 5 carbon atoms, preferably 1, 4 or 5 carbon atoms. Preferred alkyl alkanoates are methyl butyrate [apple/pineapple], ethyl butyrate [orange/pineapple], iosamyl acetate [banana/pear], pentyl butyrate [pear/apricot], pentyl pentanoate [apple], octyl acetate [orange].

Peppermint is a common flavouring for tooth whitening films. Peppermint flavouring contains menthol as well as other components such as menthone, menthofuran, cineol, pulegone, together with some lesser ingredients.

Preferably the flavouring agent is present in a proportion of from 0.1 to 10 wt. % by dry weight of the tooth whitening film, more preferably from 1 to 5 wt. % by dry weight of the tooth whitening film.

The sweetener may be a sugar substitute, such as an artificial sugar substitute or a natural sugar substitute. An artificial sugar substitute may be one or more selected from the group comprising sucralose and cyclamate aspartame, advantame, saccharin, acesulfame potassium. A natural sugar substitute may be selected from the group comprising stevia, erythritol, mannitol, sorbital and xylitol. Preferably the sweetener is sucralose.

Preferably the sweetener is present in a proportion of from 0.01 to 5 wt. % by dry weight of the tooth whitening film. More preferably the acidifier is present in a proportion of from 0.05 to 0.5 wt. % by dry weight of the tooth whitening film.

The acidifier may be an inorganic acidifier or an organic acidifier. Phosphoric acid is a preferred inorganic acidifier. Preferred organic acidifiers are those selected from the group comprising lactic acid, malic acid, acetic acid, and citric acid, with citric acid being most preferred.

Preferably the acidifier is present in a proportion of from 0.1 to 5 wt. % by dry weight of the tooth whitening film. More preferably the acidifier is present in a proportion of from 1.0 to 1.5 wt. % by dry weight of the tooth whitening film.

The antioxidant may be one or more selected from tocopherol (vitamin E), tertiary-butylhydroquinone (TBHQ), butylated hydroxyanisole (BHA), butylated hydroxytoluene and ethylenediaminetetraacetic acid or a salt thereof. A preferred antioxidant is ethylenediaminetetraacetic acid (EDTA).

Preferably the antioxidant is present in a proportion of from 0.01 to 0.5 wt. % by weight of the tooth whitening film, more preferably from 0.05 to 0.15 wt. % by dry weight of the tooth whitening film.

The chelating agent may be ethylenediaminetetraacetic acid or a salt thereof. Chelating agents can be used to sequester heavy metal ions, thereby preventing the degradation of peroxy carboxylic acids.

The chelating agent may be present in an amount of from 0.1 to 5% by weight of the dry tooth whitening film.

A preservative may also be present in the tooth whitening film. Typical preservatives may be one or more compounds selected from the group comprising potassium sorbate, benzoic acid and its salts, propionic acid and its salts, salicylic acid and its salts and triclosan.

Preferably the preservative is present in a proportion of from 0.01 to 5 wt. % by dry weight of the tooth whitening film. More preferably the preservative is present in a proportion of from 0.05 to 0.5 wt. % by dry weight of the tooth whitening film.

Also disclosed herein is a process for the manufacture of a tooth film. The film does not require the presence of further layers, such as barrier layers or supporting substrates.

The tooth whitening film is prepared from an aqueous tooth whitening liquid. The aqueous tooth whitening liquid is a mixture of the components of the tooth whitening film with water.

The non-hydrogen peroxide bleaching agent and water soluble film-forming polymer components of the tooth whitening film can be mixed with water to provide an aqueous tooth whitening liquid. The water is typically potable water. Distilled or de-ionised water may also be used. Preferably, the components are added to water under shear.

The mixing step may further comprise the addition of one or more further components of the aqueous tooth whitening film. The one or more further components may be selected from one or more of the group comprising colourant, gelling agent, flavouring, sweetener, acidifier, antioxidant and chelating agent.

The mixing parameters, such as shear force and duration, will be dependent upon the scale of the process of manufacture, as well as the component of the tooth whitening film to be mixed. This in turn will affect the choice of equipment to be employed in the mixing step.

Typically, the mixing step is initiated by adding any water soluble film-forming polymer and plasticizer into the water together with any optional gelling agent, further polymers or gums. Typically, any acidifier and any optional further components such as colourant, sweetener or other low level additives also will be added at this stage. The water soluble film-forming polymer and any other polymeric components or gums will be added in an order which prevents an early excessive viscosity build, i.e. the polymers or gums which produce the lowest viscosity build will be added first. Typically, any flavours will be mixed at the latter stages to prevent any degradation of thermally sensitive components or the loss of volatile components. At the laboratory scale, the non-hydrogen peroxide bleaching agent, such as a peroxy carboxylic acid, particularly such as a complex of PAP and polysaccharide such as dextrin, can be incorporated near the end of mixing to prevent unnecessary exposure to heat which may result in degradation. At the industrial scale, the build-up of heat during mixing is significantly reduced, and so the non-hydrogen peroxide bleaching agent, can be added at any point in the mixing step.

A laboratory scale process may involve a batch size in the range of from 50 g to 10 kg. Suitable mixing apparatus for such laboratory scale batch sizes include bench-top homogenisers such as those by Silverson Machines Ltd. or IKA England LTD and overhead stirrers, such as those by IKA England LTD. An industrial scale process may involve a batch size of greater than 10 kg, such as a batch size in the range of from 15 kg to 40 kg or more. Suitable mixing apparatus for such industrial scale batch sizes include an industrial bowl cutting machine, such as those by Kilia (Fleischerei- and Spezial-Maschinen-Fabrik GmbH).

For example, the dental bleaching agent, such as a complex of PAP and polysaccharide or a complex of hydrogen peroxide and polyvinyl pyrrolidone, can be mixed at a shear rate in the range of from 1000 to 6000 rpm. For smaller quantities on a laboratory scale, the shear rate may be in a range of from 2000 to 6000 rpm, preferably in a range of from 3000 to 4000 rpm. For larger quantities on an industrial scale, the shear rate may be in a range of from 1500 to 2500 rpm, preferably approximately 2000 rpm. The mixing time for smaller quantities on a laboratory scale can be in a range of from 5 to 20 minutes, preferably from 5 to 10 minutes. For larger quantities on an industrial scale, the mixing time may be in a range of from 10 to 20 minutes, preferably approximately 15 minutes.

Once the components are mixed with water to provide the aqueous tooth whitening liquid, it may be applied to a substrate. The aqueous tooth whitening liquid may be applied by known film-forming processes, such as dipping, spraying, knife over roller casting, extrusion and injection moulding.

A casting device may be used to apply the aqueous tooth whitening liquid to the substrate such as a caster, spreader, die or hopper. The aqueous liquid may be pumped into a spreader. If necessary, the temperature of the aqueous liquid may be held constant by heating elements in order to carefully control the viscosity of the liquid.

The spreader distributes the aqueous tooth whitening liquid homogeneously over a substrate and controls the thickness profile of the film. The spreader typically has a slot through which the aqueous tooth whitening liquid is cast. The slot is preferably designed to ensure that the hydrostatic pressure between the centre and the edges of the cast film is equilibrated. Preferably, the aqueous tooth whitening liquid is maintained at a constant temperature to ensure a constant viscosity and therefore homogenous thickness distribution of the resulting film.

Many different materials can be used for the substrate such as copper; silver plated copper; chromium plated steel; stainless steel; metal coated with polyvinyl alcohol or gelatin; paper such as silicone coated paper; or polymer films such as polyethylene, polypropylene, polyester such as polyethylene terephthalate (PET), particularly siliconized PET, polytetrafluoroethylene (PTFE) films. Preferably the substrate comprises paper, paper coated with a release layer such as silicone, polyethylene, polypropylene, polytetrafluoroethylene (PTFE) or a polyester such as polyethylene terephthalate (PET), particularly siliconized PET films.

The aqueous tooth whitening liquid carried on the substrate can then be dried. Exemplary drying methods include indirect heating, heating by radiation and air stream drying.

In one embodiment, an air feed stream with no or a low moisture content is directed towards the aqueous tooth whitening liquid on the substrate and an air exhaust stream loaded with water vapour is removed. The air exhaust stream loaded with moisture may be vented or passed to condensers for the condensation and separation of liquid water.

It is possible to dry both surfaces of the aqueous tooth whitening liquid on the substrate. This can be achieved by looping the drying tooth whitening film around a series of polished rollers and directing air feed streams to each exposed surface in turn.

The air feed stream may be at ambient temperature. Alternatively, the air feed stream may be a heated air feed stream. The bleaching agent PAP melts above 75° C. and the chemical degrades with the evolution of carbon dioxide to ε-phthalimido pentanol, such that the heated air stream should have a temperature below 60° C. Preferably, the heated air feed stream may have a temperature in the range of from greater than ambient to 60° C. More preferably, the heated air stream may have a temperature in the range of from 25° C. to 55° C., still more preferably in the range of from 45 to 55° C. The heating may be carried out in a belt heater with a belt speed in the range of from 0.2 to 2.0 m/min, and preferably at a speed in the range of from 0.5 to 1.5 m/min.

Alternatively, heated rollers or radiative heaters such as infra-red lamps may be used to dry the aqueous liquid to provide the film. These may heat the aqueous tooth whitening liquid carried on the substrate to a temperature in the range of from greater than ambient to 60° C., preferably to a temperature in the range of from 25° C. to 55° C.

The drying step may comprise first drying of a first surface of the aqueous tooth whitening liquid carried on the substrate to provide a first dried tooth whitening film carried on the substrate. The first surface of the aqueous tooth whitening liquid may be the outer surface of the liquid opposite to a second surface adjacent to the support. The first dried tooth whitening film may then be separated from the substrate. The second surface of the first dried tooth whitening film may then be second dried to provide a second dried tooth whitening film. The first and second drying may be independently carried out as discussed above.

In this way, a tooth whitening film can be provided which comprises less than 15% water by dry weight of the film. The water content is preferably in a range of from 3 to 12% by dry weight of the film, more preferably in a range of from 5 to 10% by dry weight of the film and even more preferably in a range of from 5 to 7% by dry weight of the film.

The tooth whitening film may be stored on a support, such as a plastic or paper support, particularly a paper support having a silicone release layer, although this is not required.

The tooth whitening film may be stored in sterile packaging, such as a sealed packet. The sealed packet may be water tight, and more preferably water and air tight. The packet may be made of a metallic foil such as aluminium foil, or a plastic film coated with a metallic layer.

The tooth whitening film obtainable by the method disclosed herein may be used in a method of bleaching teeth. The method may comprise at least the step of:

applying the tooth whitening film, obtained as described herein, to one or more teeth of a subject.

The method may be a cosmetic method. Preferably the method is a solely cosmetic method. As used herein, the term a "solely cosmetic method" means a cosmetic method which does not encompass the treatment or prevention of a medical condition or indication.

In the method, the tooth whitening film may first be released from its sterile packaging. Subsequently, any support is removed, for instance by peeling the tooth whitening film from the support. Once the tooth whitening film is free from any other layers, it may be applied to one or more teeth. Such an application does not require the action of a dentist, dental hygienist or dental nurse, and can be carried out by any person wishing to whiten their teeth.

The tooth whitening film provides good adhesion to tooth surfaces so that the non-hydrogen peroxide bleaching agent can act upon a tooth or teeth, while also dissolving in the oral cavity during bleaching such that subsequent removal of the film by the subject is not required. For instance, the tooth whitening film may adhere to a tooth or teeth within 10 seconds of contact. Adhesion may occur by the action of saliva on the PVP component of the film, rendering it tacky or may be as a result of the presence of an adhesive water soluble polymer. The tooth whitening film can adhere to a tooth or teeth for at least 15 minutes after contact.

The tooth whitening film can be applied to one or more teeth of a subject for a period of more than 5 minutes and less than or equal to 60 minutes, preferably for a period of from 15 to 30 minutes, after which the film disintegrates in the oral cavity due to the water solubility of the water soluble film-forming polymer component. Consequently, it is not necessary for the subject to remove the tooth whitening film after use.

As used herein, the term "film" refers to an article having dimensions defined by three mutually perpendicular axes in which two of the dimensions are larger than the third. Typically, the two larger dimensions are at least an order of magnitude greater than the smallest dimension.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

All documents mentioned in this specification are incorporated herein by reference in their entirety for all purposes.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term 'saturated' refers to an organic compound or group which does not contain any carbon-carbon bonds which are double, triple or aromatic bonds. Analogously, the term 'unsaturated' refers to an organic compound or group which contains one or more carbon-carbon bonds which are double, triple or aromatic bonds. In this context, the terms 'saturation' and 'unsaturation' do not refer to bonds between a carbon atom and a heteroatom, such as nitrogen and oxygen, such that for instance an organic compound having a carbonyl group may fall within the definition of an unsaturated organic compound.

As used herein, the term "peroxy carboxylic acid" refers to an organic compound comprising a —C(=O)—O—O—H group.

As used herein, the term "alkyl" refers to a monovalent alkane produced by the removal of a hydrogen atom. Preferably, the alkyl is a $C_{1-5}$ alkyl, more preferable a $C_{1-3}$ alkyl.

Certain aspects and embodiments of the invention will now be illustrated by way of example and with reference to the following table.

EXAMPLES

Components

Kollidon® 90 F is a polyvinyl pyrrolidone water soluble film-forming polymer having a weight average molecular weight in the range of from 1 000 000 to 1 500 000 supplied by BASF.

Klucel JF is a hydroxypropyl cellulose water soluble film-forming polymer supplied by IMCD and manufactured by Ashland Inc.

Nisso HPC-LM is a hydroxypropyl cellulose water soluble film-forming polymer supplied by Nippon Soda Co Ltd.

Eureco HC-P11 is an 11 wt. % PAP non-hydrogen peroxide bleaching agent complex with β-cyclodextrin supplied by Solvay.

Peroxydone K-90 is a dental bleaching agent formed from a complex of 16-20 wt. % hydrogen peroxide and polyvinyl pyrrolidone having a molecular weight of 1 300 000 supplied by Ashland Inc.

Pectin is a polysaccharide water soluble film-forming polymer supplied by CP Kelco.

Blanose 7LF is a sodium carboxymethyl cellulose gum water soluble film-forming polymer having a degree of substitution of 7 with a substitution range of 0.65 to 0.9 and a viscosity in the range of from 25 to 50 mPa·s for a concentration of 2% measured with a spindle #1 at 60 rpm supplied by Aqualon, a Division of Hercules Inc.

Glycerol is a plasticiser is supplied by Brenntag.

Sorbital T80 is an emulsifier also known as polysorbate 80 and is supplied by Azelis.

Peppermint is a flavouring supplied by IMCD.

Potassium sorbate is a preservative supplied by Claremont Ingredients.

Sucralose is a sweetener supplied by Azelis.

Phosphoric acid is an acidifier supplied by Sigma-Aldrich.

BHT is butylated hydroxytoluene and is an antioxidant supplied by Sigma-Aldrich.

Sodium tripolyphospate is a linear polyphosphate supplied by Brenntag.

Sodium hexametaphosphate is a cyclic polyphosphate supplied by Brenntag.

EXPERIMENTAL

A variety of tooth whitening films are prepared through a one-pot process described below. The mass of the components of each sample film, by dry weight, is provided in Table 1 below. Table 2 shows a full characterisation of the composition of Example 1 (Batch number DEV04533) in terms of the aqueous tooth whitening liquid by weight and as component proportions for the wet liquid ("wet weight") and the corresponding composition without water ("dry weight"), together with the composition of the corresponding tooth whitening film, both as produced after drying (6 wt. % water content) and after complete water removal ("complete dryness").

Comparative examples 1 and 2 are either free from polyphosphate or contain only linear polyphosphate without cyclic polyphosphate. Examples 1-3 are Examples of the invention which contain sodium hexametaphosphate and optionally sodium tripolyphosphate.

Thin films of Comparative Example 2 and Examples 1-3 corresponding to the compositions of Batch Numbers DEV04536, DEV04533, DEV4534 and DEV04535 respectively contain a combination of PVP (Kollidon 90 F), ε-phthalimido peroxy hexanoic acid β-cyclodextrin complex (Eureco HC-P11), sodium carboxymethyl cellulose (Blanose 7 LF), glycerol, sorbital (sorbital T80), flavouring, sweetener, preservative, acidifier and polyphosphate.

All liquid ingredients including water were weighed directly into a suitable sized stainless-steel pot. All solids were weighed individually into weigh boats. Water was present in an amount of 72.33% by weight, with the compositions provided in Table 1 forming the remaining 27.67% by weight.

Sucralose, BHT and potassium sorbate were added directly to the stainless-steel pot alongside SHMP (sodium hexametaphosphate) and Prayphos STPP FG GR SP (sodium tripolyphosphate). The mixture was agitated using an Ultra Turrax UT-50 high shear mixer for two minutes at speed 2. Klucel was added over six minutes at speed 3. Kollidon was added over eleven minutes at speed 3.5, Blanose 7LF was added over two minutes at speed 3.5. Eureco was added over five minutes and thirty seconds at speed 3.5. A final mix of the resulting mixture was carried out at speed 4 for two minutes. The mixture was degassed for 30 minutes. The coating knife, Sheen instrument (S285638, 1117/250 mm), is set at a height that affords a suitable thickness of the final film (between 250 microns and 1500 microns). A suitable substrate (PET or paper) is placed on the film applicator (1133N Sheen automatic film applicator) the knife is placed over the substrate. The casting liquid is spread in front of the knife and the applicator casts the liquid uniformly onto the paper. The paper is then placed in BioFilm's proprietary oven hood to dry and is periodically rotated to ensure its dries evenly. The sheet was cut in to 60×20 mm strips and the average weight of ten strips was found to be within specified limits.

TABLE 1

Dental bleaching film formulations

| INGREDIENT | Example 1 DEV04533 Dry weight (w/w %) | Example 2 DEV04534 Dry weight (w/w %) | Example 3 DEV04535 Dry weight (w/w %) | Comparative Example 1 non-H2O2 Dry weight (w/w %) | Comparative Example 2 DEV04536 Dry weight (w/w %) |
|---|---|---|---|---|---|
| Kollidon 90F | 40% | 39% | 40% | 44% | 40% |
| Klucel JF | 26% | 25% | 26% | 28% | 26% |
| Eureco HC-P11 | 10.1% | 10.1% | 10.1% | 10.1% | 10.1% |
| Blanose 7LF | 5% | 5% | 5% | 5% | 5% |
| Glycerol | 4% | 3% | 4% | 4% | 4% |
| Sorbital T80 | 2% | 2% | 2% | 2% | 2% |
| Peppermint flavouring | 4% | 4% | 4% | 4% | 4% |
| Sucralose | 0.1% | 0.1% | 0.1% | 0.1% | 0.1% |
| Potassium sorbate | 0.1% | 0.1% | 0.1% | 0.1% | 0.1% |

TABLE 1-continued

| Dental bleaching film formulations | | | | | |
|---|---|---|---|---|---|
| INGREDIENT | Example 1 DEV04533 Dry weight (w/w %) | Example 2 DEV04534 Dry weight (w/w %) | Example 3 DEV04535 Dry weight (w/w %) | Comparative Example 1 non-H2O2 Dry weight (w/w %) | Comparative Example 2 DEV04536 Dry weight (w/w %) |
| Phosphoric acid | 1% | 1% | 1% | 1% | 1% |
| BHT | 0.1% | 0.1% | 0.1% | 0.1% | 0.1% |
| Sodium tripolyphosphate | 3.5% | 5% | 0% | 0% | 7% |
| Sodium hexametaphosphate | 3.5% | 5% | 7% | 0% | 0% |
| TOTAL | 100% | 100% | 100% | 100% | 100% |

TABLE 2

| Characterisation of Example 1 (DEV04533) | | | | | |
|---|---|---|---|---|---|
| INGREDIENT | Aqueous tooth whitening liquid (g) | Aqueous tooth whitening liquid Dry weight (w/w %) | Aqueous tooth whitening liquid Wet weight (w/w %) | Film weight (mg) at complete dryness | Film weight (mg) at 6% water content |
| Kollidon 90F | 4.5498 | 40.32% | 11.02% | 58.46 | 54.95 |
| Klucel JF | 2.9073 | 25.76% | 7.04% | 37.36 | 35.12 |
| Eureco HC-P11 | 1.1397 | 10.10% | 2.76% | 14.64 | 13.76 |
| Blanose 7LF | 0.5664 | 5.02% | 1.37% | 7.28 | 6.84 |
| Glycerol | 0.4065 | 3.60% | 0.98% | 5.22 | 4.91 |
| Sorbital T80 | 0.2449 | 2.17% | 0.59% | 3.15 | 2.96 |
| Peppermint flavouring | 0.4954 | 4.39% | 1.20% | 6.36 | 5.98 |
| Sucralose | 0.0102 | 0.09% | 0.02% | 0.13 | 0.12 |
| Potassium sorbate | 0.0147 | 0.13% | 0.04% | 0.19 | 0.18 |
| Phosphoric acid | 0.1501 | 1.33% | 0.36% | 1.93 | 1.81 |
| BHT | 0.0102 | 0.09% | 0.02% | 0.13 | 0.12 |
| Sodium tripolyphosphate | 0.3950 | 3.50% | 0.96% | 5.08 | 4.77 |
| Sodium hexametaphosphate | 0.3950 | 3.50% | 0.96% | 5.08 | 4.77 |
| Water | 30.00 | — | 72.67% | | 8.70 |
| TOTAL | 41.285 | 100.00% | 100.00% | 145.00 | 145.00 |

Two further films utilising a different dental bleaching agent were prepared according to the formulations shown in Table 3 as discussed in the experimental section above. These films designated as Example 4 and Comparative Example 3 were prepared with hydrogen peroxide complexed with polyvinyl pyrrolidone (Peroxydone K-90) as the bleaching agent to provide 6 wt. % hydrogen peroxide equivalent by dry weight.

TABLE 3

| Dental bleaching formulations | | |
|---|---|---|
| INGREDIENT | Comparative Example 3 (6 wt. % $H_2O_2$) Dry weight (w/w %) | Example 4 DEV04537 (6 wt. % $H_2O_2$) Dry weight (w/w %) |
| Peroxydone K-90 | 41% | 41% |
| Pectin | 41% | 35% |
| Glycerol | 11% | 10% |
| Peppermint Liquid | 5% | 5% |
| Polysorbate 80 | 2% | 2% |
| Sucralose | 0.2% | 0.2% |
| Sodium tripolyphosphate | 0.0% | 3.5% |
| Sodium hexametaphosphate | 0.0% | 3.5% |
| TOTAL | 100.0% | 100.0% |

Extrinsic Stain Removal

The films prepared according to the formulations shown in Table 1 and Table 3 were tested for their ability to remove extrinsic stains from bovine teeth. The test method utilizes bovine tooth specimens that are incubated over a 2-week period in staining broth with daily broth changes and toothbrushing to form a tenacious brown stain on the tooth surface that is comparable to human extrinsic tooth stain.

The extrinsic stain removal method used in this investigation was a modification and improvement of that described by Stookey et al. In vitro removal of stain with dentifrices. *J Dent Res* 61(11):1236-1239, November 1982.

Bovine permanent teeth, obtained from an abattoir, were used to prepare test specimens. The test specimens comprised 4-mm squares of bovine tooth enamel mounted in 1.5-cm square acrylic blocks. The tooth squares were removed using a diamond cutting disk under wet conditions to prevent thermal damage to the enamel during the cutting process. Using a mold, each tooth square was embedded in self-curing dental acrylic to provide a 1.5-cm square block with the labial enamel surface facing upward. This was done in such a manner that the areas of tooth substance exposed by the cutting process were sealed by the acrylic, while the 4-mm square of surface enamel was left exposed. The finished tooth specimens were examined under a dissecting microscope, and they were discarded if they had imperfections. The top surface of the polyester blocks is ground flush with the leveled labial surface of the enamel squares by means of a dental model trimmer. The surface was then smoothed by hand-sanding on 400 grit emery paper using water as the lubricant until all grinding marks were removed. Finally, the top surface of each tooth specimen was hand-polished to a mirror finish using a water slurry of calcined kaolin (median particle size=1.2 micrometer) on a cotton cloth. The finished tooth specimens were examined under a dissecting microscope and discarded if any imperfections in the enamel surface were observed. Acceptable specimens were thoroughly rinsed with distilled water and refrigerated in a humidor until ready for stain formation.

In preparation for the formation of artificial stained pellicle on the enamel, the specimens were etched for 60 seconds in 0.2M HCl, followed by a 30-second immersion in a saturated solution of sodium carbonate. A final etch was performed with 1% phytic acid for 60 seconds, after which the specimens were rinsed with deionized water and attached to the staining apparatus.

The staining apparatus was designed to provide alternate immersion into the staining broth and air-drying of the specimens. The apparatus consisted of an aluminum platform base which supports a Teflon rod (1.9 cm in diameter) connected to an electric motor, which by means of a speed reduction box, rotates the rod at a constant rate of 1.5 rpm. Threaded screw holes were spaced at regular intervals along the length of the rod. Tooth specimens were attached to the rod by means of plastic screws in threaded screw holes in the back of an acrylic mount, then the tooth specimens were screwed onto the rod. Beneath the rod was a removable, 300 mL capacity trough, which held the staining broth.

The staining broth was prepared by adding 1.02 g of instant coffee, 1.02 g of instant tea, and 0.75 g of porcine gastric mucin (Nutritional Biochemicals Corporation, Cleveland, OH, US) to 250 mL of sterilized trypticase soy broth. Approximately 50 mL of a 24-hour *Micrococcus luteus* culture was also added to the stain broth. The apparatus, with tooth specimens attached and the staining broth in the trough was then placed in an incubator at 37° C. with the specimens rotating continuously through the staining broth and air.

The staining broth was replaced once every 24 hours for 10 consecutive days. With each broth change, the trough and specimens were brushed and rinsed with deionized water to remove any loose deposits. On the eleventh day, the staining broth was modified by the addition of 0.03 g of $FeCl_3 \cdot 6H_2O$, and this was continued with daily broth changes until the stained pellicle film on the specimens was sufficiently dark (L* measurement of 30-35). Then, the specimens were removed from the staining broth, brushed thoroughly with deionized water, placed in a humidor, and refrigerated until used.

In preparation for treatment the specimens were stratified into equal groups of 10 specimens each, with each group having equivalent average baseline L*a*b* stain scores. Treatments were designed to simulate daily applications with whitening products in accordance with manufacturer's instructions.

Each simulated day consisted of the following: Prior to strip application, the tooth specimens were manually brushed with water for 10 seconds; then a single drop of artificial saliva was placed on the tooth surface. A piece of the strip was cut out and positioned over the tooth specimen, and another drop of artificial saliva was applied to the backside of the piece. The strip was left on the tooth specimen for 30 minutes and a drop of artificial saliva was added every 5 minutes. Water rinses were performed after each procedure. Tooth specimens were stored in water between treatments. After treatment all tooth specimens were rinsed thoroughly with water.

The entire procedure above was repeated 14 times to simulate 14 days of treatment. Spectrophotometer readings were made at baseline and after 3, 7, and 14 treatment applications.

Color and intensity of stained pellicle (extrinsic stain specimens) on the teeth were measured before and after treatment by taking diffuse reflectance absorbance readings with a Minolta CM-503i spectrophotometer (Minolta Camera Co., NJ, US) equipped with diffuse illumination, an 8° viewing angle, and 3-mm aperture. Absorbance measurements over the entire visible color spectrum were obtained using the tristimulus L*a*b* color space established by the Commission Internationale de L'Eclairage (CIE) "Recommendations on uniform color spaces. Color difference equations. Psychometric color terms." Suppl. 2 to CIE publication 15 (E-13.1) 1971/(TC-1.3), 1978, Paris: Bureau Central de la CIE, 1978. Measurements were conducted using a targeting mask to align the center of the 4-mm square segment of exposed enamel directly over the 3-mm diameter targeting aperture, which enabled accurate positioning of the specimens each time. Three absorbance readings, using the L*a*b* scale, were taken across each tooth specimen.

The primary outcome variable to assess efficacy was the overall change in extrinsic stain (E), and was calculated using the CIELAB equation (1) show below:

$$E = \left[(L^*)^2 + (a^*)^2 + (b^*)^2\right]^{1/2} \quad (1)$$

L*, a*, and b* represent the stain removal measurements for the individual components of the L*a*b* scale. These components indicate the specific changes in whiteness (L*), red-green color axis (a*), and yellow-blue color axis (b*), and they were also analyzed separately. The difference between the pre-test and post-test readings for each color factor (L*, a*, and b*) represents the ability of the test products to reduce existing extrinsic stain (i.e. stained pellicle) and thereby increase tooth whiteness. Data were tabulated using a standard spreadsheet program (Excel™, Microsoft Corporation, Redmond, WA, US).

Tooth specimens were read after blotting them dry and allowing them to air-dry at room temperature for 1 minute. When the specimens were exposed to air for long periods of time, the color parameters change dramatically, thus exposure time was kept to a minimum to reduce dehydration and the need for subsequent rehydration. The difference between the pre-test and post-test readings for each color factor (L*, a*, and b*) represent the ability of the test product to modify intrinsic tooth color or to remove extrinsic stain from the teeth. The changes in tooth color were compared using the color difference equation 2:

$$\Delta E = \left[(\Delta L^*)^2 + (\Delta a^*)^2 + (\Delta b^*)^2\right]^{1/2} \quad (2)$$

The symbols ΔL*, Δa*, and Δb* represent the changes in white-black, red-green, and yellow-blue, respectively. The individual components of the L*a*b* scale were also analyzed separately to determine the color range most affected by the treatments, specifically changes in the whiteness (L*), red-green color axis (a*), and yellow-blue color axis (b*). The greater the value for the calculated ΔE, the greater is the color change of the teeth (e.g. increased whiteness of the teeth), and thus the greater is the reduction in extrinsic stain on the teeth.

The efficacy analysis was based on data from evaluable teeth, defined as all tooth specimens that received treatments with study products, had pre-treatment stain measurement and had all post-baseline data points for overall change in extrinsic stain (i.e. ΔE).

Statistical tests were performed using an Analysis of Variance model of changes from baseline in component tooth color scores (L*, a*, b*) with treatment as a factor. Comparisons between treatment groups were made using the Student Newman-Keuls test for each primary and secondary efficacy variable. Descriptive statistics (e.g. mean and standard deviation) are presented by treatment group.

The primary efficacy endpoint was the overall score change from baseline in extrinsic stain (ΔE) after 14 simulated days of treatment. The results are shown in Table 4.

After just 3 treatment applications, all whitening strip products produced significant increases in L* relative to group 4 (Comparative Example 2; DEVO 4536), which changed little from baseline. The a* and b* parameters did not result in significant changes compared to the control. Groups 1, 3 and 5 (Examples 1, 3 and 4; DEVO 4533, 4535 and 4537) had ΔE means that were significantly greater than group 4, while groups 2 (Example 2; DEVO 4534) had numerically better ΔE, but did not attain statistical significance.

After 7 treatment applications, all whitening strip products again provided significant increases in L* relative to group 4 (Comparative Example 2; DEVO 4536). The changes from baseline, yielded ΔE means that were significantly different from group 4. In addition, the treatment effects, as indicated by both L* and b* were more pronounced for group 5 (Example 4; DEVO 4537) than the remaining groups. In addition, the ΔE means for group 5 was also significant.

The relationships between groups after 14 treatment applications paralleled those that were observed after 7 applications, but the changes were more prominent. The treatment effects, as determined by changes from baseline (Table 4), for group 5 (Example 4; DEVO 4537) was significantly greater than the rest of the groups.

Except for group 4 (Comparative Example 2; DEVO 4536), all whitening strip products reduced the intensity of existing extrinsic stain accumulations at all measurement intervals, namely after 3, 7, and 14 treatment applications. The strip with the greatest whitening efficacy, and the most highly significant from the rest, was Group 5 (Example 4, DEVO 4537), while Groups 1 (Example 1, DEV04533) and 7 were statistically significant from Groups 2, 3, 4 (Example 2; DEVO 4534, Example 3; DEVO 4535 and Comparative Example 2, DEVO 4536) and group 6.

Figure 2:
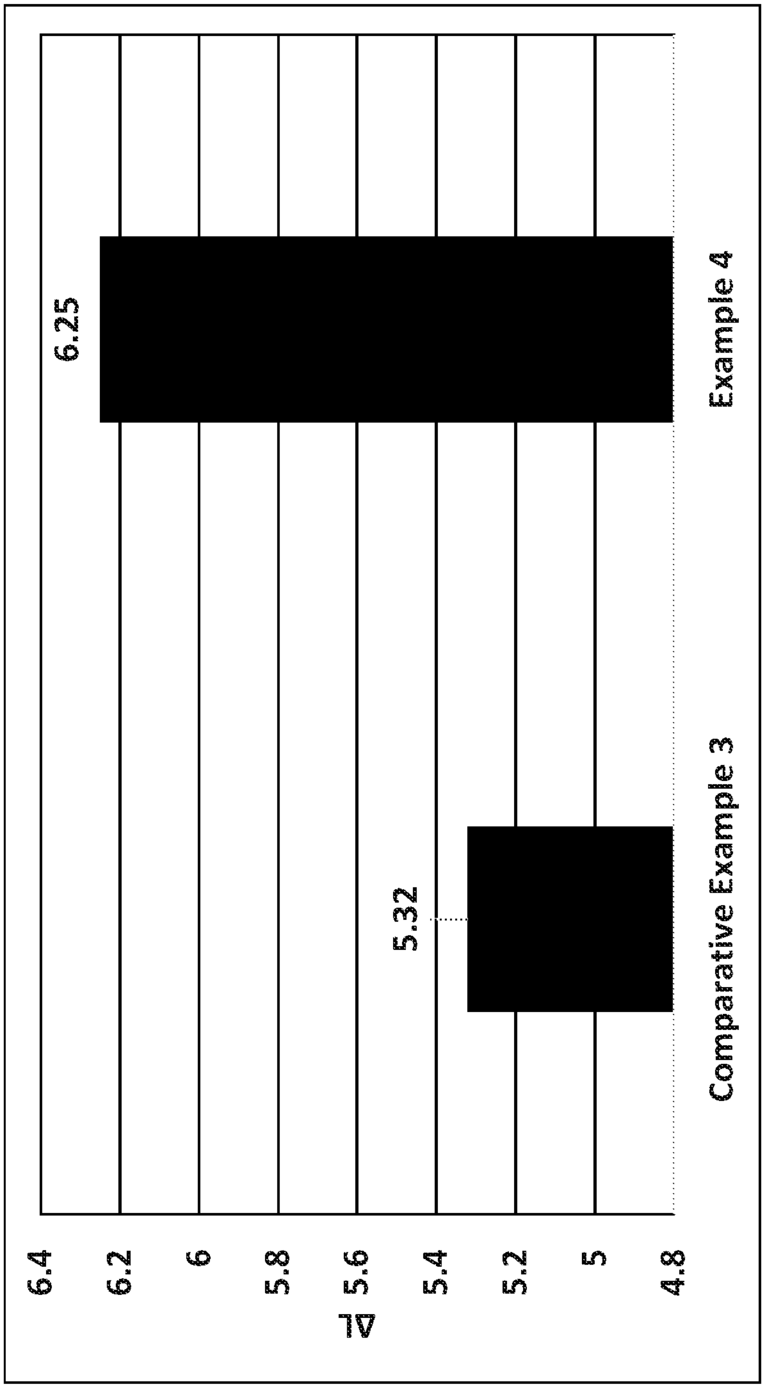
FIG. 2 shows a chart of the change in the extrinsic stain on teeth after 14 applications of a tooth whitening film containing polyphosphates according to Example 4 of the invention compared to Comparative Example 3 which is free of polyphosphate, for formulations in which the bleaching agent was a complex of hydrogen peroxide with polyvinyl pyrrolidone.

The change in lightness (L) from the baseline value after 14 applications are shown in FIGS. 1 and 2.

TABLE 4

Efficacy of extrinsic stain removal

| Group | Sample | Change in extrinsic stain on teeth after 14 applications with whitening strips † | | | |
|---|---|---|---|---|---|
| | | ΔL* | Δa* | Δb* | ΔE |
| 1 | Example 1 (DEVO 4533) | 4.90 ± 1.05 $^{D}$ | −0.04 ± 1.60 $^{B}$ | 3.32 ± 2.75 $^{B}$ | 6.45 ± 1.99 $^{C}$ |
| 2 | Example 2 (DEVO 4534) | 3.07 ± 1.54 $^{C}$ | −0.05 ± 0.61 $^{B}$ | 2.43 ± 1.66 $^{AB}$ | 4.26 ± 1.55 $^{B}$ |
| 3 | Example 3 (DEVO 4535) | 3.23 ± 1.09 $^{C}$ | 0.07 ± 1.43 $^{B}$ | 3.72 ± 2.54 $^{B}$ | 5.40 ± 2.07 $^{BC}$ |
| 4 | Comparative Example 2 (DEVO 4536) | 0.42 ± 0.92 $^{A}$ | −0.44 ± 1.01 $^{B}$ | 0.51 ± 0.82 $^{A}$ | 1.61 ± 0.59 $^{A}$ |
| 5 | Example 4 (DEVO 4537) | 6.25 ± 1.33 $^{E}$ | −1.16 ± 1.16 $^{AB}$ | 6.36 ± 2.33$^{C}$ | 9.09 ± 2.57 $^{D}$ |
| 6 | Comparative Example 1 | 2.23 ± 0.48 $^{B}$ | −0.83 ± 1.15 $^{AB}$ | 2.02 ± 0.82 $^{AB}$ | 3.37 ± 0.67 $^{AB}$ |
| 7 | Comparative Example 3 | 5.32 ± 1.13 $^{DE}$ | −2.03 ± 0.63 $^{AB}$ | 3.68 ± 1.30 $^{AB}$ | 6.65 ± 1.27 $^{C}$ |

† Mean score ± standard deviation, n = 10.

Values in the same column with the same superscript letter are not statistically different, while those with different superscript letters are different at $p < 0.05$ based on ANOVA and 2-Tail SNK Test.

Comparative Example 1 shows the change in lightness for a control formulation in which the non-peroxide bleaching agent is PAP and which is absent of polyphosphate. The addition of 7% by weight cyclic polyphosphate as shown in Example 3 improves the efficacy of a whitening film strip from an increase in lightness of 2.23 for Comparative Example 1 to 3.23 for Example 3.

The film of Comparative Example 2 contains 7% by weight of a linear polyphosphate rather than the 7% by weight of cyclic polyphosphate of Example 3. The film of Comparative Example 2 exhibits a poorer improvement in lightness compared to Comparative Example 1 which is free of polyphosphate and Example 3 which contains an equivalent amount of cyclic polyphosphate.

The film of Example 2 increases the total polyphosphate content to 10% by weight of the film, in which 5% by weight is cyclic polyphosphate and 5% by weight is linear polyphosphate. This provides an improved increase of lightness compared to the film of Comparative Example 1 in which no polyphosphate is present and compared to the film of Comparative Example 2 which contains 7% by weight linear polyphosphate. Thus, reducing the concentration of linear polyphosphate below 7% by weight in the presence of cyclic polyphosphate leads to an increase in lightness.

The film of Example 1 has a reduced total polyphosphate content of 7% by weight compared to the 10% by weight total phosphate content of Example 2, such that both the cyclic and linear polyphosphates are present at 3.5% by weight of the film, providing a 7% by weight total polyphosphate content equivalent to that of Example 3. Example 1 shows a significant increase in the change in lightness of 4.90, compared to that of 3.07 of Example 2 and that of 2.23 of Comparative Example 1.

These films were tested for their ability to remove extrinsic stains from bovine teeth using the test method discussed above. The change in lightness (L) from the baseline value after 14 applications is shown in FIG. 1.

It is apparent from a comparison of Examples 1 and 3 that for a similar total amount of polyphosphate (7% by weight of the dry film), a combination of cyclic and linear polyphosphates provides improved bleaching. It is also apparent from a comparison of Examples 1 and 2 that when both cyclic and linear polyphosphates are present in the film, decreasing the amount of both polyphosphates from 5% by weight to 3.5% by weight leads to an increase reduction in lightness improvement. Thus, a synergistic effect of the combination of cyclic and linear polyphosphates at about 3.5% by weight of each component is apparent.

The films of Comparative Example 3 and Example 4 utilise hydrogen peroxide in a hydrogen peroxide polymer complex as the dental bleaching agent, rather than a non-hydrogen peroxide dental bleaching agent as in Examples 1-3 and Comparative Examples 1 and 2.

These films were tested for their ability to remove extrinsic stains from bovine teeth using the test method discussed above. The change in lightness (L) from the baseline value after 14 applications is shown in FIG. 2.

The film of Comparative Example 3 does not contain any polyphosphate, while that of Example 4 contains 3.5% by weight of both a cyclic and linear polyphosphate resulting in 7% by weight total polyphosphate content. Example 4 shows a significant increase in the change in lightness of 6.25, compared to that of 5.32 for Comparative Example 3 which is free from polyphosphate but has a similar amount of non-hydrogen peroxide bleaching agent.

Improved Stain Resistance

Two films prepared according to the formulations shown in Table 1 were tested for their ability to impart stain resistance to teeth.

The test method utilizes hydroxy apatite (HA) discs which are pre-treated to form a pellicle layer and then stained.

Pellicle Layer Formation

Artificial saliva was made using an in-house method. Water (200 mL) was added to a 1000 mL beaker containing a magnetic stir bar. The magnetic stirrer was set at 250 rpm. NaCl (0.40 g), KCl (0.40 g), $NaH_2PO_4 \cdot H_2O$ (0.78 g) and Urea were added and dissolved. Once completely dissolved a further portion of water (750 mL) was added to the beaker. $CaCl \cdot 2H_2O$ was separately dissolved in water (50 mL) and then added to the 1000 mL beaker. The pH of the artificial saliva solution was then adjusted to 6 by use of HCl or NaOH buffer solutions. A 500 mL sample of the artificial saliva mix was then taken, and to which was added porcine gastric mucin (PGM) (1.25 g). PGM was added in 4 parts, mixing with a magnetic stirrer bar at 950 rpm for approximately 15 minutes after each addition and for 90 minutes after the final addition, to yield a cloudy, slightly yellow solution of PGM/artificial saliva mixture (2.5 g/L concentration). HA discs were polished on one side using 240 grit silicon carbide paper and the colour of the polished side measured using a colourimeter. Each disc was placed polished side up in a petri dish and either PGM/artificial saliva mixture was added to the dish. The dishes were covered with a lid and placed in an oven overnight at 37° C. for 18 hours. The discs were then removed and patted dry with paper towel, and the colour measured again before use.

Staining Broth Recipe and Preparation

Preparation of staining broth: Nescafe Gold Blend coffee (1 g) was dissolved in boiling water (100 mL) in a 150 mL beaker and stirred with magnetic stirrer bar at 350 rpm for 5 mins. A single Tetley tea bag was added to boiling water (100 mL) in a 150 mL beaker and stirred with magnetic stirrer bar at 350 rpm for 5 mins. The tea and coffee solutions were added together in a 500 mL beaker. Concentrated blueberry juice (30 mL) was then added to tea/coffee solution. PGM (0.75 g) was then added to staining broth in three parts after each addition the staining broth was agitated with a magnetic stirrer bar at 950 rpm for 15 minutes, and for 90 minutes after the final addition.

HA discs were each placed in their own petri dish polished side up. The staining broth was added to the dishes until each disc was fully submerged, taking care to avoid pouring the broth straight onto the surface of the discs. The petri dishes were covered with lids, labelled, and put into the oven at 37° C. for approximately 72 hours.

The stained hydroxy apatite discs were exposed to ten treatments with a film according to Comparative Example 1 which utilised a PAP non-hydrogen peroxide bleaching agent and was free from polyphosphate or were exposed to ten treatments with a film according to Example 1 which utilised a PAP non-hydrogen peroxide bleaching agent and 3.5% by weight of both cyclic and linear polyphosphate providing 7% by weight total polyphosphate content.

Pre-treated hydroxy apatite discs which stain to a lesser extent, as represented by a lower ΔL % value indicate an improvement in stain resistance.

Figure 3:
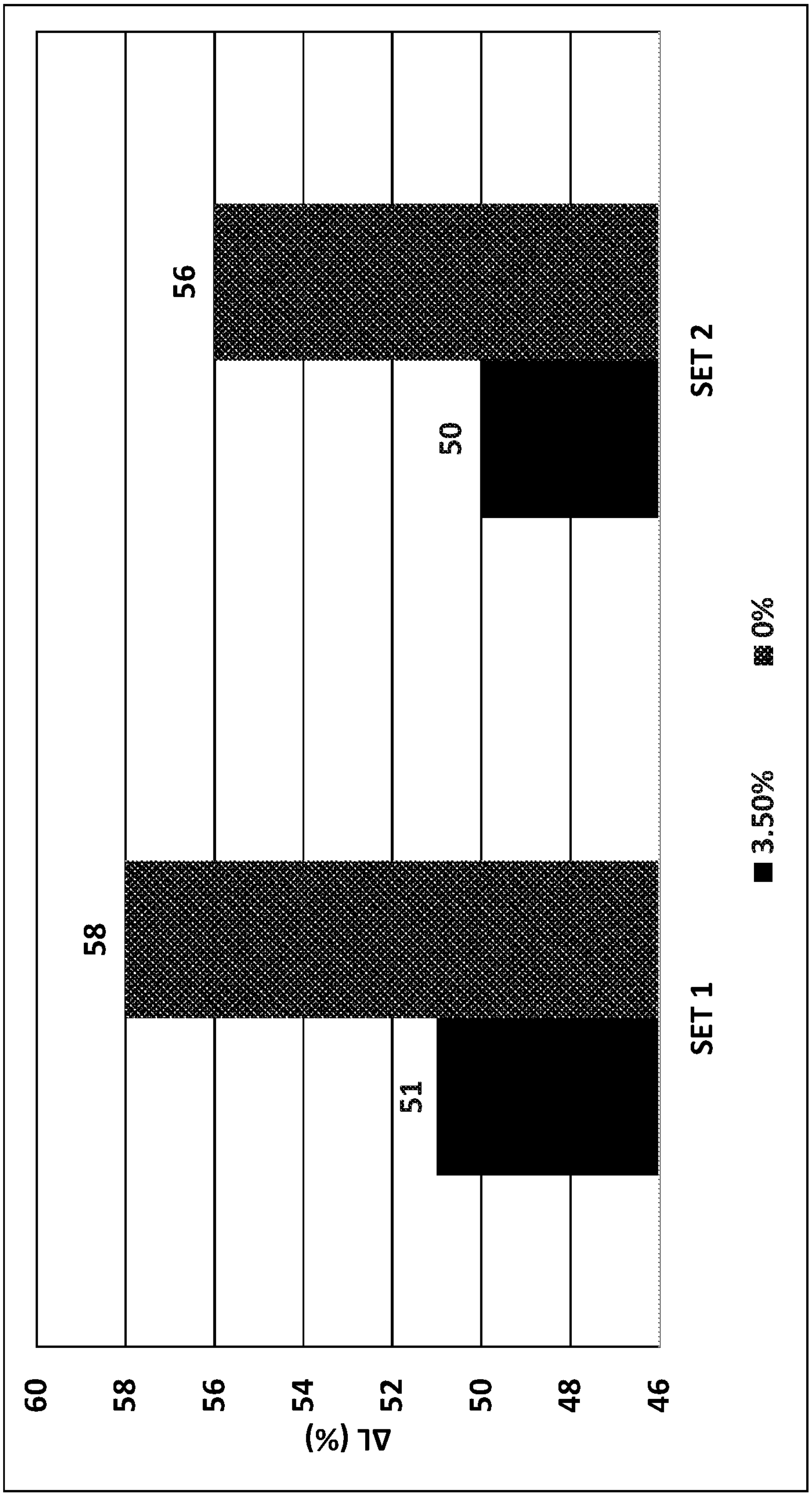
FIG. 3 shows a chart of the percentage change in the extrinsic stain on teeth after 10 applications of a tooth whitening film containing polyphosphates according to Example 1 of the invention compared to Comparative Example 1 which is free of polyphosphate, for formulations in which the non-hydrogen peroxide bleaching agent was PAP.

It is apparent from a comparison of the change in lightness shown in FIG. 3 that the inclusion of 3.5% by weight of both cyclic and linear polyphosphate according to the formulation of Example 1 resulted in the hydroxy apatite discs staining less than non-phosphate containing Comparative Example 1.

Tooth Whitening Films for Dental Aligners

A variety of tooth whitening films for use with dental aligners were prepared through a one-pot process. The mass of the components of each sample film, by dry weight, is provided in Table 5 below.

Thin films of Examples 5 and 6 corresponding to the compositions of Batch Numbers 19061 and 19088 respectively contain a combination of hydrogen peroxide complexed with polyvinyl pyrrolidone (Peroxydone K-90) as the bleaching agent and water soluble film-forming polymer respectively, glycerol plasticizer, polysorbate 80 emulsifier, peppermint flavouring, sucralose sweetener and polyphosphates to provide about 7.4 wt. % hydrogen peroxide equivalent by dry weight.

Thin films of Example 7 corresponding to the composition of Batch Number 19059 contain a combination of PVP (Kollidon 90 F) and hydroxypropyl cellulose (HPC-LM) water soluble film-forming polymers, ε-phthalimido peroxy hexanoic acid (PAP) β-cyclodextrin complex (Eureco HC-P11) bleaching agent, sodium carboxymethyl cellulose (Blanose 7 LF) as water soluble film-forming polymer, glycerol plasticizer, sorbital T80 emulsifier, peppermint flavouring, sucralose sweetener, potassium sorbate preservative, phosphoric acid acidifier, BHT antioxidant and polyphosphates to provide about 1.1 wt. % PAP bleaching agent by dry weight.

All liquid ingredients including water were weighed directly into a suitable sized stainless-steel pot. All solids were weighed individually into weigh boats. Water was present in an amount of 82.04% by weight, with the compositions provided in Table 5 forming the remaining 17.96% by weight for Examples 5 and 6. Water was present in an amount of 72.67% by weight, with the composition provided in Table 5 forming the remaining 27.33% by weight for Example 7.

Sucralose, and where present BHT and potassium sorbate were added directly to the stainless-steel pot alongside sodium hexametaphosphate and sodium tripolyphosphate. The mixture was agitated using an Ultra Turrax UT-50 high shear mixer for two minutes at speed 2. Hydroxypropyl cellulose (HPC-LM), if present, was added over six minutes at speed 3. Kollidon, if present, was added over eleven minutes at speed 3.5, Blanose 7LF, if present, was added over two minutes at speed 3.5. Eureco, if present, was added over five minutes and thirty seconds at speed 3.5. A final mix of the resulting mixture was carried out at speed 4 for two minutes. The mixture was degassed for 30 minutes. The coating knife, Sheen instrument (S285638, 1117/250 mm), is set at a height that affords a suitable thickness of the final film (between 250 microns and 1500 microns). A suitable substrate (PET or paper) is placed on the film applicator (1133N Sheen automatic film applicator) the knife is placed over the substrate. The casting liquid is spread in front of the knife and the applicator casts the liquid uniformly onto the paper. The paper is then placed in BioFilm's proprietary oven hood to dry and is periodically rotated to ensure its dries evenly. The sheet was cut into the desired dimensions shown in Table 6 and the average weight of ten strips was found to be within specified limits.

TABLE 5

Dental bleaching film formulations for use with dental aligners

| INGREDIENT | Example 5 19061 (7.43 wt. % $H_2O_2$) Dry weight (w/w %) | Example 6 19088 (7.43 wt. % $H_2O_2$) Dry weight (w/w %) | Example 7 19059 (1.1 wt. % PAP) Dry weight (w/w %) |
|---|---|---|---|
| Pectin | 35.06% | 35.05% | |
| Peroxydone K90 | 41.29% | 41.29% | |
| Kollidon 90F | — | — | 40.31% |
| HPC-LM | — | — | 25.77% |
| Eureco HC-P11 | — | — | 10.10% |
| Blanose 7LF | — | — | 5.02% |
| Glycerol | 9.59% | 9.59% | 3.60% |
| Polysorbate 80 | 2.26% | 2.26% | 2.17% |
| Peppermint flavouring | 4.58% | 4.58% | 4.39% |
| Sucralose | 0.20% | 0.20% | 0.09% |
| Potassium sorbate | — | — | 0.13% |
| Phosphoric acid | — | — | 1.33% |
| BHT | — | — | 0.09% |
| Sodium tripolyphosphate | 3.51% | 3.51% | 3.50% |
| Sodium hexametaphosphate | 3.51% | 3.51% | 3.50% |
| TOTAL | 100% | 100% | 100% |

To assess the impact of the aligner on the dissolution characteristics of the films in vivo, samples of the films from each of the batches were applied to the top teeth and the time taken for the films to dissolve, with and without the presence of a clear dental aligner, recorded.

TABLE 6

Dental bleaching film dimensions and dissolution times

| EXAMPLE | Dimensions Length × width (mm) | Thickness (μm) | Mass (mg) | Dissolution time without aligner (min) | Dissolution time with aligner (min) |
|---|---|---|---|---|---|
| Example 5 | 60 × 20 | 72 | 113 | 9 | 75+ |
| Example 6 | 58 × 15 | 104 | 94 | 26 | 90+ |
| Example 7 | 58 × 15 | 125 | 115 | 18 | 60+ |
| Example 7 | 60 × 20 | 125 | 152 | 20 | 60+ |

It is apparent from the dissolution times shown in Table 6 that the presence of a dental aligner significantly increased the dissolution time of the strip. Without wishing to be bound by theory, it is believed that this is due to the presence of the aligner providing a barrier to the passage of saliva to the dental bleaching film, leading to a reduction in the quantity of saliva available to dissolve the film.

It was found that dental bleaching films having the thicknesses shown in Table 6 allowed the immediate application of the dental aligner after the strip had been applied to teeth. Strips with a width of above 15 mm were found to be less preferred because they were too wide, leading to the excess film having to be folder over the top and around the back of the teeth, leading to difficulties in adhering the film to teeth. The narrower films with a width of 15 mm were found to be easier to shape on to teeth and provide a faster adhesion. As a result of this study, dental bleaching films with a thickness in the range of from 50 to 150 micrometers, preferably from 60 to 130 micrometers and more preferably from 70 to 125 micrometers and a width of from 10 to 12 mm are preferred for use with a dental aligner.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope of the appended claims. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A tooth whitening film comprising:

a dental bleaching agent comprising hydrogen peroxide in a hydrogen peroxide-polymer complex, said hydrogen peroxide present in a total amount of 0.01% to 35% by weight; and one or more polyphosphates in a total amount of from 7% to 10% by weight to provide at least one of enhanced bleaching or improved stain resistance, said one or more polyphosphates comprising:

one or more cyclic polyphosphates of formula (II) in an amount of from 3% to 6% by weight:

(II)

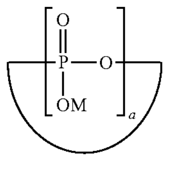

wherein a is a whole number from 3 to 10 and M is selected from one or more of the group comprising hydrogen and an alkali metal; and one or more linear polyphosphates of formula (III) in an amount of from 3% to 4% by weight:

(III)

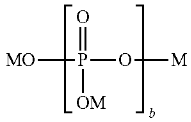

wherein b is a whole number from 2 to 5 and M is selected from one or more of the group comprising hydrogen and an alkali metal.

2. The film of claim 1, wherein the hydrogen peroxide-polymer complex comprises a hydrogen peroxide-polyvinyl pyrrolidone complex.

3. The film of claim 1, wherein the one or more cyclic polyphosphates comprise sodium hexametaphosphate.

4. The film of claim 1, wherein the one or more cyclic polyphosphates are present in a total amount of 7% to 9% by weight.

5. The film of claim 1, wherein the linear polyphosphate comprises sodium tripolyphosphate.

6. The film of claim 1, wherein the one or more polyphosphates comprise sodium hexametaphosphate and sodium tripolyphosphate.

7. The film of claim 1, further comprising a water soluble film-forming polymer in a total amount of 40% to 95% by weight, wherein the water soluble film-forming polymer comprises one or more of a polyvinyl pyrrolidone, polyacrylic acid or a salt thereof, polyalkylene glycol in which the alkylene group has 2 or 3 carbon atoms and copolymers thereof, and a polysaccharide.

8. The film of claim 1, further comprising one or more plasticizers in a total amount of 0.1% to 15% by weight, wherein the one or more plasticizers are selected from the group comprising a polyol.

9. The film of claim 1, further comprising one or more emulsifiers in a total amount of 0.1% to 10% by weight, wherein the one or more emulsifiers are selected from the group comprising a fatty acid derivative, a lecithin and a polysorbate.

10. The film of claim 1, further comprising water in an amount of from 0.1% to 12% by weight.

11. The film of claim 1, wherein the tooth whitening film further comprises one or more further components selected from the group comprising colourant, gelling agent, flavouring, sweetener, antioxidant, acidifier and chelating agent.

12. The film of claim 11, which satisfies one or more of the following conditions:

the colourant is FD & C blue no. 1 or lakes thereof;

the gelling agent is selected from the group comprising a polysaccharide and a hydrocolloid adhesive agent;

the flavouring is selected from the group comprising menthol, peppermint and an alkyl alkanoates, in which the alkyl is straight chained or branched and comprises from 1 to 8 carbon atoms, and the alkanoate group comprises from 1 to 5 carbon atoms;

the sweetener is one or more of the group comprising aspartame, acelfame k, sucralose, cyclamate, erythritol, mannitol, sorbital and xylitol;

the antioxidant is one or more selected from the group comprising tocopherol, tertiary-butylhydroquinone, butylated hydroxyanisole, butylated hydroxytoluene and ethylenediaminetetraacetic acid or a salt thereof;

the acidifier is phosphoric acid; and the chelating agent is ethylenediaminetetraacetic acid or a salt thereof.

13. The film of claim 1, for use with a dental aligner, wherein the film has a thickness from 50 μm to 500 μm.

14. The film of claim 1, wherein the one or more plasticizers comprise glycerol, polyalkylene glycol, polyalkylene glycol monomethyl ether, monosaccharide, oligosaccharide, sorbital and sorbitan, in which the alkylene groups are independently selected from $C_{1-5}$ alkylene.

15. The film of claim 1, wherein the tooth whitening film comprises the one or more polyphosphates without a barrier layer.

16. A tooth whitening film comprising:

a dental bleaching agent comprising hydrogen peroxide present in a total amount of 0.01% to 35% by weight in a hydrogen peroxide-polymer complex comprising a hydrogen peroxide-polyvinyl pyrrolidone complex present in a proportion of from 0.01 to 80% by dry weight of the tooth whitening film;

one or more polyphosphates in a total amount of from 3% to 10% by weight, said one or more polyphosphates comprising:

one or more cyclic polyphosphates of formula (II) in an amount of from 3% to 6% by weight:

(II)

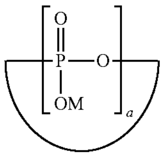

wherein a is a whole number from 3 to 10 and M is selected from one or more of the group comprising hydrogen and an alkali metal; and one or more linear polyphosphates of formula (III) in an amount of from 3% to 4% by weight:

(III)

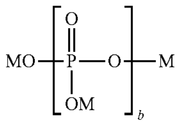

wherein b is a whole number from 2 to 5 and M is selected from one or more of the group comprising hydrogen and an alkali metal;

one or more water soluble film-forming polymers in a total amount of 40% to 95% by weight;

one or more plasticizers in a total amount of 0.1% to 15% by weight; and one or more emulsifiers in a total amount of 0.1% to 10% by weight, wherein the film has a thickness from 50 μm to 500 μm.

17. The tooth whitening film of claim 16, wherein the hydrogen peroxide is 14.4% by dry weight of the film and polyvinyl pyrrolidone is 65.6% by dry weight of the film.

18. The tooth whitening film of claim 16, wherein the hydrogen peroxide-polyvinyl pyrrolidone complex is present in a proportion of from 10 to 70% by dry weight of the tooth whitening film.

19. The tooth whitening film of claim 16, wherein the hydrogen peroxide-polyvinyl pyrrolidone complex is present in a proportion of from 20 to 60% by dry weight of the tooth whitening film.

20. The film of claim 1, wherein the one or more linear polyphosphates may be present in a total amount of about 3.5% by weight, and wherein the one or more cyclic polyphosphates may be present in a total amount of about 3.5% by weight.

* * * * *